United States Patent
Rafii-Tari

(10) Patent No.: US 11,793,580 B2
(45) Date of Patent: Oct. 24, 2023

(54) SYSTEMS AND METHODS FOR LOCATION SENSOR-BASED BRANCH PREDICTION

(71) Applicant: Auris Health, Inc., Redwood City, CA (US)

(72) Inventor: Hedyeh Rafii-Tari, Mountain View, CA (US)

(73) Assignee: Auris Health, Inc., Redwood City, CA (US)

(*) Notice: Subject to any disclaimer, the term of this patent is extended or adjusted under 35 U.S.C. 154(b) by 101 days.

(21) Appl. No.: 17/137,952

(22) Filed: Dec. 30, 2020

(65) Prior Publication Data
US 2021/0113279 A1  Apr. 22, 2021

Related U.S. Application Data

(63) Continuation of application No. 16/424,165, filed on May 28, 2019, now Pat. No. 10,905,499.
(Continued)

(51) Int. Cl.
*A61B 34/20* (2016.01)
*A61B 34/30* (2016.01)
(Continued)

(52) U.S. Cl.
CPC .......... *A61B 34/20* (2016.02); *G06T 7/0012* (2013.01); *G16H 20/40* (2018.01);
(Continued)

(58) Field of Classification Search
CPC .......... A61B 34/20; A61B 2034/2051; A61B 2090/3983; A61B 2090/397; A61B 34/30;
(Continued)

(56) References Cited

U.S. PATENT DOCUMENTS

| 4,745,908 A | 5/1988 | Wardle |
| 5,273,025 A | 12/1993 | Sakiyama et al. |

(Continued)

FOREIGN PATENT DOCUMENTS

| CN | 101147676 A | 3/2008 |
| CN | 101222882 A | 7/2008 |

(Continued)

OTHER PUBLICATIONS

CN 2nd office action for appl No. 201980003362, dated Jun. 16, 2021, 4 pages.
(Continued)

*Primary Examiner* — Carolyn A Pehlke
(74) *Attorney, Agent, or Firm* — Chang & Hale LLP

(57) ABSTRACT

Provided are systems and methods for location sensor-based branch prediction. In one aspect, the method includes determining a first orientation of an instrument based on first location data generated by a set of one or more location sensors for the instrument and determining a second orientation of the instrument at a second time based on second location data. A distal end of the instrument is located within a first segment of a model at the first time and the second time and the first segment branches into two or more child segments. The method also includes determining data indicative of a difference between the first orientation and the second orientation and determining a prediction that the instrument will advance into a first one of the child segments based on the data indicative of the difference.

30 Claims, 27 Drawing Sheets

Related U.S. Application Data

(60) Provisional application No. 62/678,962, filed on May 31, 2018, provisional application No. 62/678,160, filed on May 30, 2018.

(51) Int. Cl.
*G16H 20/40* (2018.01)
*G06T 7/00* (2017.01)

(52) U.S. Cl.
CPC .............. *A61B 2034/2051* (2016.02); *A61B 2034/2065* (2016.02); *A61B 2034/301* (2016.02)

(58) Field of Classification Search
CPC ...... A61B 2034/301; A61B 2034/2065; A61B 1/00149; A61B 5/062; A61B 2034/107; A61B 34/10; A61B 2034/105; A61B 34/37; A61B 1/2676; A61B 34/71; A61B 1/00006; A61B 1/00009; A61B 90/37; A61B 2017/00809; A61B 2090/364; A61B 34/35; A61B 5/061; A61B 5/065; A61B 17/00234; A61B 1/0051; A61B 2034/102; A61B 34/32; A61B 34/00; G06T 2207/10068; G06T 7/0012; G06T 2207/30004; G06T 2207/30061; G06T 2200/24; G06T 7/0014; G06T 7/74; G06T 19/003

See application file for complete search history.

(56) References Cited

U.S. PATENT DOCUMENTS

| | | | |
|---|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells et al. |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,167,292 A | 12/2000 | Badano et al. |
| 6,203,493 B1 | 3/2001 | Ben-Haim |
| 6,246,784 B1 | 6/2001 | Summers et al. |
| 6,246,898 B1 | 6/2001 | Vesely et al. |
| 6,332,089 B1 | 12/2001 | Acker et al. |
| 6,425,865 B1 | 7/2002 | Salcudean et al. |
| 6,466,198 B1 | 10/2002 | Feinstein |
| 6,490,467 B1 | 12/2002 | Bucholz et al. |
| 6,553,251 B1 | 4/2003 | Lähdesmäki |
| 6,665,554 B1 | 12/2003 | Charles et al. |
| 6,690,963 B2 | 2/2004 | Ben-Haim et al. |
| 6,690,964 B2 | 2/2004 | Bieger et al. |
| 6,812,842 B2 | 11/2004 | Dimmer |
| 6,899,672 B2 | 5/2005 | Chin et al. |
| 6,926,709 B2 | 8/2005 | Bieger et al. |
| 7,180,976 B2 | 2/2007 | Wink et al. |
| 7,206,627 B2 | 4/2007 | Abovitz et al. |
| 7,233,820 B2 | 6/2007 | Gilboa |
| 7,386,339 B2 | 6/2008 | Strommer et al. |
| 7,756,563 B2 | 7/2010 | Higgins et al. |
| 7,850,642 B2 | 12/2010 | Moll et al. |
| 7,901,348 B2 | 3/2011 | Soper et al. |
| 8,155,403 B2 | 4/2012 | Tschirren et al. |
| 8,190,238 B2 | 5/2012 | Moll et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa et al. |
| 8,929,631 B2 | 1/2015 | Pfister et al. |
| 9,014,851 B2 | 4/2015 | Wong et al. |
| 9,125,639 B2 | 9/2015 | Mathis et al. |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar et al. |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State et al. |
| 10,285,574 B2 | 5/2019 | Landey et al. |
| 10,299,870 B2 | 5/2019 | Connolly et al. |
| 10,524,866 B2 | 1/2020 | Srinivasan et al. |
| 2001/0021843 A1 | 9/2001 | Bosselmann et al. |
| 2001/0039421 A1 | 11/2001 | Heilbrun et al. |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard et al. |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0186349 A1 | 9/2004 | Ewers et al. |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger et al. |
| 2005/0085714 A1 | 4/2005 | Foley et al. |
| 2005/0107679 A1 | 5/2005 | Geiger et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0197557 A1 | 9/2005 | Strommer et al. |
| 2005/0256398 A1 | 11/2005 | Hastings et al. |
| 2005/0272975 A1 | 12/2005 | McWeeney et al. |

(56) References Cited

U.S. PATENT DOCUMENTS

| | | |
|---|---|---|
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0058643 A1 | 3/2006 | Florent et al. |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0156019 A1 | 7/2007 | Larkin et al. |
| 2007/0167743 A1 | 7/2007 | Honda et al. |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani et al. |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0147089 A1 | 6/2008 | Loh et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari et al. |
| 2009/0054729 A1 | 2/2009 | Mori et al. |
| 2009/0076476 A1 | 3/2009 | Barbagli et al. |
| 2009/0149867 A1 | 6/2009 | Glozman et al. |
| 2009/0209817 A1 | 8/2009 | Averbuch |
| 2009/0227861 A1 | 9/2009 | Ganatra et al. |
| 2009/0248036 A1 | 10/2009 | Hoffman et al. |
| 2009/0259230 A1 | 10/2009 | Khadem et al. |
| 2009/0262109 A1 | 10/2009 | Markowitz et al. |
| 2009/0292166 A1 | 11/2009 | Ito et al. |
| 2009/0295797 A1 | 12/2009 | Sakaguchi |
| 2010/0008555 A1 | 1/2010 | Trumer et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0113852 A1 | 5/2010 | Sydora |
| 2010/0121139 A1 | 5/2010 | OuYang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg et al. |
| 2010/0240989 A1 | 9/2010 | Stoianovici et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0054303 A1 | 3/2011 | Barrick et al. |
| 2011/0092808 A1 | 4/2011 | Shachar et al. |
| 2011/0184238 A1 | 7/2011 | Higgins et al. |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0065481 A1 | 3/2012 | Hunter et al. |
| 2012/0069167 A1 | 3/2012 | Liu et al. |
| 2012/0071782 A1 | 3/2012 | Patil et al. |
| 2012/0082351 A1 | 4/2012 | Higgins et al. |
| 2012/0120305 A1 | 5/2012 | Takahashi |
| 2012/0165656 A1 | 6/2012 | Montag et al. |
| 2012/0191079 A1 | 7/2012 | Moll et al. |
| 2012/0209069 A1 | 8/2012 | Popovic et al. |
| 2012/0215094 A1 | 8/2012 | Rahimian et al. |
| 2012/0219185 A1 | 8/2012 | Hu et al. |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2013/0060146 A1 | 3/2013 | Yang et al. |
| 2013/0144116 A1 | 6/2013 | Cooper et al. |
| 2013/0165945 A9 | 6/2013 | Roelle et al. |
| 2013/0204124 A1 | 8/2013 | Duindam et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0303892 A1 | 11/2013 | Zhao et al. |
| 2013/0345718 A1 | 12/2013 | Crawford et al. |
| 2014/0058406 A1 | 2/2014 | Tsekos |
| 2014/0107390 A1 | 4/2014 | Brown et al. |
| 2014/0114180 A1 | 4/2014 | Jain |
| 2014/0142591 A1 | 5/2014 | Alvarez et al. |
| 2014/0148808 A1 | 5/2014 | Inkpen et al. |
| 2014/0180063 A1 | 6/2014 | Zhao et al. |
| 2014/0235943 A1 | 8/2014 | Paris et al. |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0296655 A1 | 10/2014 | Akhbardeh et al. |
| 2014/0309527 A1 | 10/2014 | Namati et al. |
| 2014/0343416 A1 | 11/2014 | Panescu et al. |
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0164594 A1 | 6/2015 | Romo et al. |
| 2015/0164596 A1 | 6/2015 | Romo et al. |
| 2015/0223725 A1 | 8/2015 | Engel et al. |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265368 A1 | 9/2015 | Chopra et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter et al. |
| 2015/0313503 A1 | 11/2015 | Seibel et al. |
| 2015/0335480 A1 | 11/2015 | Alvarez et al. |
| 2016/0000302 A1 | 1/2016 | Brown et al. |

(56) References Cited

U.S. PATENT DOCUMENTS

| | | |
|---|---|---|
| 2016/0000414 A1 | 1/2016 | Brown et al. |
| 2016/0000520 A1 | 1/2016 | Lachmanovich et al. |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson et al. |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman et al. |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc et al. |
| 2016/0331469 A1 | 11/2016 | Hall et al. |
| 2016/0360947 A1 | 12/2016 | Iida et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0055851 A1 | 3/2017 | Al-Ali |
| 2017/0079725 A1 | 3/2017 | Hoffman et al. |
| 2017/0079726 A1 | 3/2017 | Hoffman et al. |
| 2017/0084027 A1 | 3/2017 | Mintz et al. |
| 2017/0100199 A1 | 4/2017 | Yu et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra et al. |
| 2017/0202627 A1 | 7/2017 | Sramek et al. |
| 2017/0209073 A1 | 7/2017 | Sramek et al. |
| 2017/0215808 A1 | 8/2017 | Shimoi et al. |
| 2017/0215969 A1 | 8/2017 | Zhai et al. |
| 2017/0238807 A9 | 8/2017 | Vertikov |
| 2017/0258366 A1 | 9/2017 | Tupin, Jr. et al. |
| 2017/0290631 A1 | 10/2017 | Lee et al. |
| 2017/0296032 A1 | 10/2017 | Li |
| 2017/0296202 A1 | 10/2017 | Brown |
| 2017/0325896 A1 | 11/2017 | Donhowe et al. |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055582 A1 | 3/2018 | Krimsky |
| 2018/0098690 A1 | 4/2018 | Iwaki |
| 2018/0177556 A1 | 6/2018 | Noonan |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083183 A1 | 3/2019 | Moll et al. |
| 2019/0086349 A1 | 3/2019 | Nelson et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117176 A1 | 4/2019 | Walker et al. |
| 2019/0117203 A1 | 4/2019 | Wong et al. |
| 2019/0125164 A1 | 5/2019 | Roelle et al. |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365209 A1 | 12/2019 | Ye et al. |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0022767 A1 | 1/2020 | Hill et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0188043 A1 | 6/2020 | Yu et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |

FOREIGN PATENT DOCUMENTS

| | | |
|---|---|---|
| CN | 102316817 A | 1/2012 |
| CN | 102458295 A | 5/2012 |
| CN | 102973317 A | 3/2013 |
| CN | 103735313 A | 4/2014 |
| CN | 105511881 A | 4/2016 |
| CN | 105559850 A | 5/2016 |
| CN | 105559886 A | 5/2016 |
| CN | 106170265 A | 11/2016 |
| CN | 106455908 A | 2/2017 |
| CN | 106455908 A | 2/2017 |
| CN | 106821498 A | 6/2017 |
| CN | 104931059 B | 9/2018 |

(56) References Cited

FOREIGN PATENT DOCUMENTS

| EP | 3025630 A1 | 6/2016 |
|---|---|---|
| KR | 20140009359 A | 1/2014 |
| RU | 2569699 C2 | 11/2015 |
| WO | 2005087128 A1 | 9/2005 |
| WO | 2009097461 A1 | 8/2009 |
| WO | 2015089013 A1 | 6/2015 |
| WO | 2017048194 A1 | 3/2017 |
| WO | 2017049163 A1 | 3/2017 |
| WO | 2017066108 A1 | 4/2017 |
| WO | 2017167754 A1 | 10/2017 |
| WO | 2019231895 A1 | 12/2019 |
| WO | PCTUS2019034145 | 12/2019 |

OTHER PUBLICATIONS

Advisory Action for U.S. Appl. No. 16/424,165, dated Apr. 15, 2020, 2 pages.
Al-Ahmad et al., dated 2005, Early experience with a computerized robotically controlled catheter system. Journal of Interventional Cardiac Electrophysiology, 12:199-202, 4 pages.
Ciuti et al., 2012, Intra-operative monocular 3D reconstruction for image-guided navigation in active locomotion capsule endoscopy. Biomedical Robotics And Biomechatronics (Biorob), 4th IEEE Ras & Embs International Conference On IEEE, 7 pages.
Fallavoliita et al., 2010, Acquiring multiview C-arm images to assist cardiac ablation procedures, EURASIP Journal on Image and Video Processing, vol. 2010, Article ID 871408, pp. 1-10.
Final Rejection for U.S. Appl. No. 16/424,165, dated Feb. 5, 2020, 10 pages.
Gutierrez et al., Mar. 2008, A practical global distortion correction method for an image intensifier based x-ray fluoroscopy system, Med. Phys, 35(3):997-1007, 11 pages.
Haigron et al., 2004, Depth-map-based scene analysis for active navigation in virtual angioscopy, IEEE Transactions on Medical Imaging, 23( 11 ): 1380-1390, 11 pages.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available athttp://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pages.
Hansen Medical, Inc. dated 2009, Sensei X Robotic Catheter System, product brochure, 3 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
International search report and written opinion dated Aug. 15, 2019 for PCT/US2019/034145, 10 pages.
Kiraly et al., 2002, Three-dimensional Human Airway Segmentation Methods for Clinical Virtual Bronchoscopy, Acad Radio!, 9:1153-1168, 16 pages.
Kiraly et al., Sep. 2004, Three-dimensional path planning for virtual bronchoscopy, IEEE Transactions on Medical Imaging, 23(9):1365-1379, 15 pages.
Konen et al., 1998, The VN-project endoscopic image processing for neurosurgery, Computer Aided Surgery, 3:1-6 , 6 pages.
Kumar et al., 2014, Stereoscopic visualization of laparoscope image using depth information from 3D model, Computer methods and programs in biomedicine 113(3):862-868, 7 pages.
Livatino et al., 2015, Stereoscopic visualization and 3-D technologies in medical endoscopic teleoperation, IEEE, 11 pages.
Luo et al., 2010, Modified hybrid bronchoscope tracking based on sequential monte carlo sampler: Dynamic phantom validation, Asian Conference on Computer Vision. Springer, Berlin, Heidelberg, 13 pages.

Marrouche et al., dated May 6, 2005, AB32-1, Preliminary human experience using a novel robotic catheter remote control. Heart Rhythm, 2(5):S63, 1 page.
Mayo Clinic, Robotic Surgery, https://www.mayoclinic.org/tests-procedures/robotic-surgery/about/pac- 20394974?p=1, Townloaded from the internet on Jul. 12, 2018, 2 pgs.
Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.
Nadeem et al., 2016, Depth Reconstruction and Computer-Aided Polyp Detection in Optical Colonoscopy Video Frames, arXiv preprint arXiv:1609.01329.
Non-Final Rejection for U.S. Appl. No. 16/424,165, dated Aug. 29, 2019, 7 pages.
Notice of Allowance for U.S. Appl. No. 16/424,165, dated Dec. 18, 2020, 2 pages.
Notice of Allowance for U.S. Appl. No. 16/424,165, dated May 13, 2020, 8 pages.
Notice of Allowance for U.S. Appl. No. 16/424,165, dated Sep. 4, 2020, 5 pages.
Oh et al., dated May 2005, P5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventionail radiology suite, AJR, 189:W357-W364, 8 pages.
Reddy et al., May 2005, P1-53. Porcine pulmonary vein ablation using a novel robotic catheter control system and real-time integration of CT imaging with electroanatomical mapping, Hearth Rhythm, 2(5):S121, 1 page.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813, 13 pages.
Shi et al., Sep. 14-18, 2014, Simultaneous catheter and environment modeling for trans-catheter aortic valve implantation, IEEE/RSJ International Conference on Intelligent Robots and Systems, pp. 2024-2202.
Slepian, dated 2010, Robotic Catheter Intervention: the Hansen Medical Sensei Robot Catheter System, PowerPoint presentation, 28 pages.
Soiheim et ai., May 14, 2009, Navigated resection of giant intracranial meningiomas based on intraoperative 30 ultrasound, Acta Neurochir, 151:1143-1151.
Solomon et al., Dec. 2000, Three-dimensional CT-Guided Bronchoscopy With a Real-Time Electromagnetic Position Sensor A Comparison of Two Image Registration Methods, Chest, 118(6):1783-1787, 5 pages.
Song et al., 2012, Autonomous and stable tracking of endoscope instrument tools with monocular camera, Advanced Intelligent Mechatronics (AIM), 2012 IEEE-ASME International Conference on IEEE, 6 pages.
Vemuri et al., Dec. 2015, Inter-operative biopsy site relocations in endoluminal surgery, IEEE Transactions on Biomedical Engineering, Institute of Electrical and Electronics Engineers, < 10 .1109/ T8ME 2015.2503981 >, 13 pages.
Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12, 1 pages.
Wilson et al., 2008, a buyer's guide to electromagnetic tracking systems for clinical applications, Proc. of SPCI, 6918:691828-1 p. 69188-11.
Yip et al., 2012, Tissue tracking and registration for image-guided surgery, IEEE transactions on medical imaging 31 ( 11 ):2169-2182, 14 pages.
Zhou et al., 2010, Synthesis of stereoscopic views from monocular endoscopic videos, Compute Vision and Pattern Recognition Workshops (CVPRW), 2010 IEEE Computer Society Conference on IEE, 8 pages.

(56) References Cited

OTHER PUBLICATIONS

CN Search Report dated Oct. 30, 2020 for CN Patent Appl. No. 20198003362.7, 12 pages.
EP Search Report for U.S. Appl. No. 19/810,868, dated Feb. 1, 2022, 10 pages.
JP Office Action for Appl. No. 2020566601, dated Sep. 6, 2022, 3 pages.

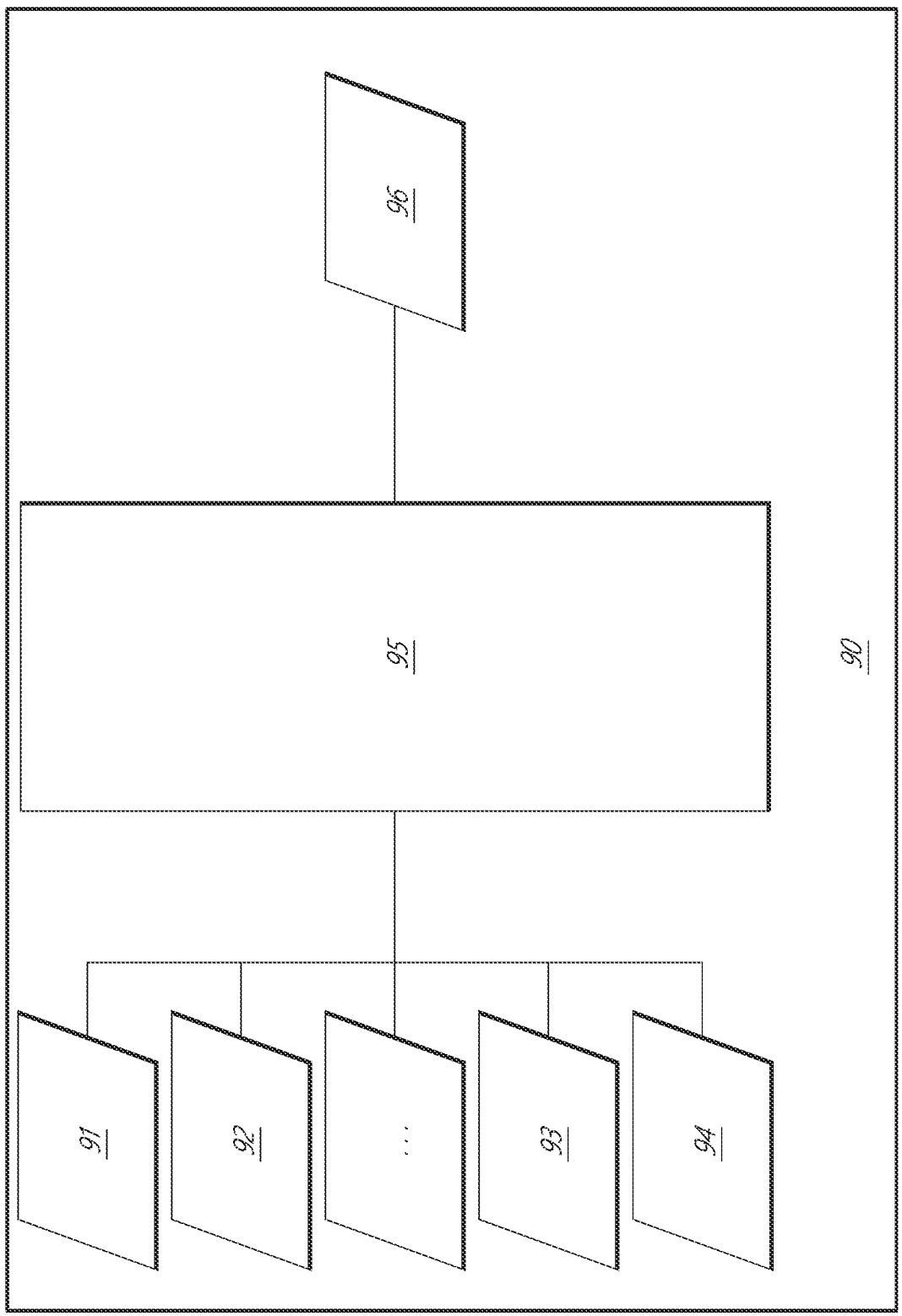

SYSTEMS AND METHODS FOR LOCATION SENSOR-BASED BRANCH PREDICTION

CROSS-REFERENCE TO RELATED APPLICATIONS

This application is a continuation of U.S. patent application Ser. No. 16/424,165, filed May 28, 2019, which claims the benefit of U.S. Provisional Application No. 62/678,160, filed May 30, 2018, and the benefit of U.S. Provisional Application No. 62/678,962, filed May 31, 2018, each of which is hereby incorporated by reference in its entirety.

TECHNICAL FIELD

The systems and methods disclosed herein are directed to branch prediction in a luminal network, and more particularly to techniques for predicting which branch an instrument will be advanced into based on location sensor data.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure. The surgical robotic system may further comprise location sensor(s) configured to generate location data indicative of a position of the distal end of the medical tool.

The surgical robotic system may further comprise one or more displays for providing an indication of the location of the distal end of the instrument to a user and thereby aid the user in navigating the instrument through the patient's luminal network. The system may be configured to perform various techniques in support of the navigation of the instrument, including predicting into which branch of the luminal network the instrument is most likely to be advanced from a current branch.

SUMMARY

The systems, methods and devices of this disclosure each have several innovative aspects, no single one of which is solely responsible for the desirable attributes disclosed herein.

In one aspect, there is provided a system, comprising a processor and at least one computer-readable memory in communication with the processor and having stored thereon a model of a luminal network of a patient, the memory further having stored thereon computer-executable instructions to cause the processor to: determine a first orientation of an instrument based on first location data generated by a set of one or more location sensors for the instrument, the first location data being indicative of the location of the instrument in a location sensor coordinate system at a first time; determine a second orientation of the instrument at a second time based on second location data generated by the set of location sensors, a distal end of the instrument being located within a first segment of the model at the first time and the second time and the first segment branching into two or more child segments; determine data indicative of a difference between the first orientation and the second orientation; and determine a prediction that the instrument will advance into a first one of the child segments based on the data indicative of the difference.

In another aspect, there is provided a non-transitory computer readable storage medium having stored thereon instructions that, when executed, cause at least one computing device to: determine a first orientation of an instrument based on first location data generated by a set of one or more location sensors for the instrument, the first location data being indicative of the location of the instrument in a location sensor coordinate system at a first time; determine a second orientation of the instrument at a second time based on second location data generated by the set of location sensors, a distal end of the instrument being located within a first segment of a model at the first time and the second time and the first segment branching into two or more child segments, the model being stored in a memory and modelling a luminal network of a patient; determine data indicative of a difference between the first orientation and the second orientation; and determine a prediction that the instrument will advance into a first one of the child segments based on the data indicative of the difference.

In yet another aspect, there is provided method of predicting movement of an instrument, comprising: determining a first orientation of an instrument based on first location data generated by a set of one or more location sensors for the instrument, the first location data being indicative of the location of the instrument in a location sensor coordinate system at a first time; determining a second orientation of the instrument at a second time based on second location data generated by the set of location sensors, a distal end of the instrument being located within a first segment of a model at the first time and the second time and the first segment branching into two or more child segments, the model being stored in a memory and modelling a luminal network of a patient; determining data indicative of a difference between the first orientation and the second orientation; and determining a prediction that the instrument will advance into a first one of the child segments based on the data indicative of the difference.

In still yet another aspect, there is provided a system, comprising a processor and at least one computer-readable memory in communication with the processor and having stored thereon a model of a luminal network of a patient, the memory further having stored thereon computer-executable instructions to cause the processor to: determine an orientation of an instrument with respect to the model based on location data generated by a set of one or more location sensors for the instrument, a distal end of the instrument being located within a first segment of the model and the first segment branching into two or more child segments; determine an orientation a first one of the child segments; and determine a prediction that the instrument will advance into the first child segment based on the orientation of the instrument and the orientation of the first child segment.

In another aspect, there is provided non-transitory computer readable storage medium having stored thereon instructions that, when executed, cause at least one computing device to: determine an orientation of an instrument with respect to a model based on location data generated by a set of one or more location sensors for the instrument, the model being stored in a memory and modelling a luminal network of a patient, a distal end of the instrument being located within a first segment of the model and the first segment branching into two or more child segments; determine an orientation a first one of the child segments; and determine a prediction that the instrument will advance into the first child segment based on the orientation of the instrument and the orientation of the first child segment.

In yet another aspect, there is provided a method of predicting movement of an instrument, comprising: determining an orientation of an instrument with respect to a model based on location data generated by a set of one or more location sensors for the instrument, the model being stored in a memory and modelling a luminal network of a patient, a distal end of the instrument being located within a first segment of the model and the first segment branching into two or more child segments; determining an orientation a first one of the child segments; and determining a prediction that the instrument will advance into the first child segment based on the orientation of the instrument and the orientation of the first child segment.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 depicts a block diagram illustrating a localization system that estimates a location of one or more elements of the robotic systems of FIGS. 1-10, such as the location of the instrument of FIGS. 13 and 14, in accordance to an example embodiment.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
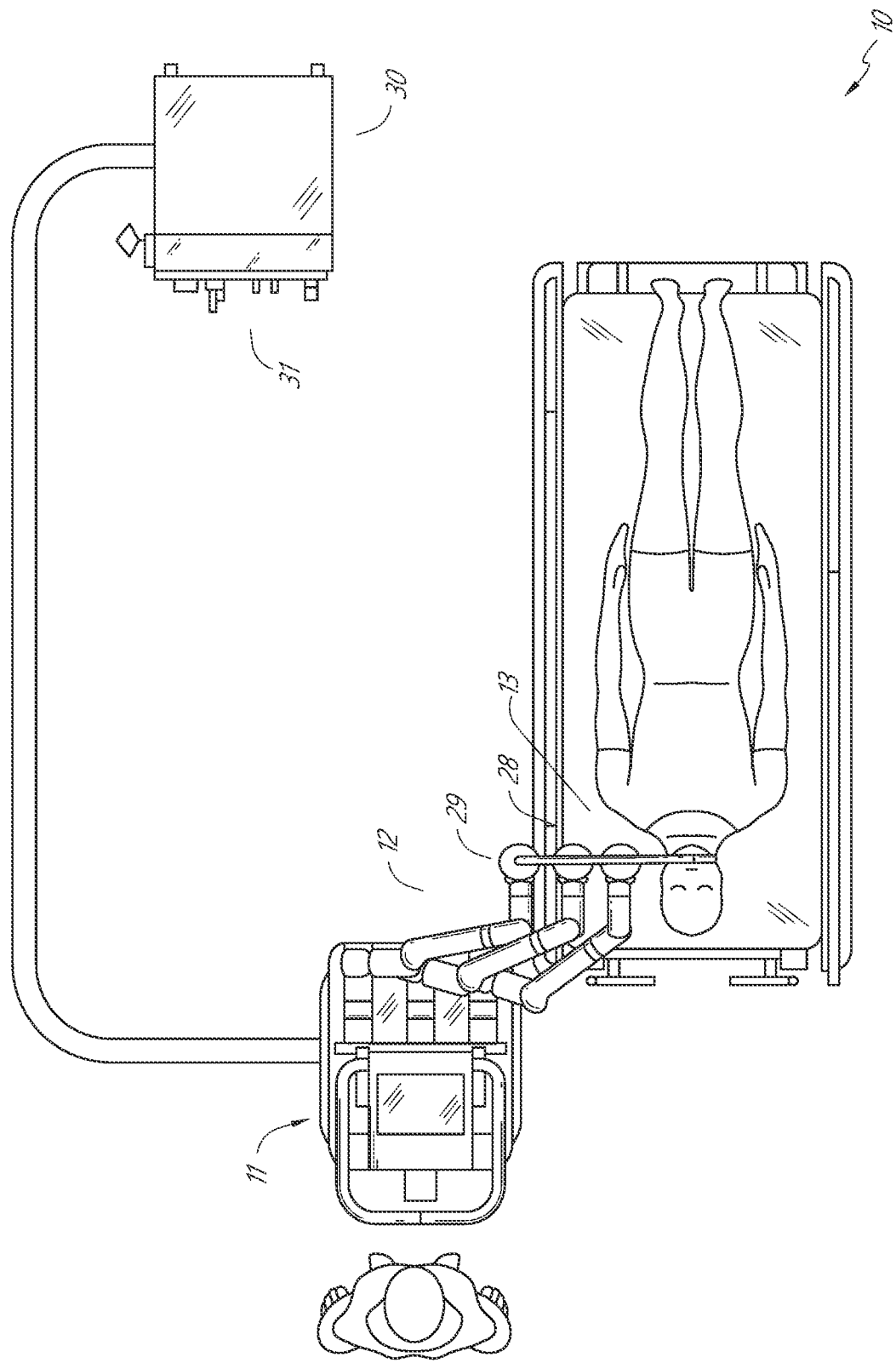
FIG. 1 illustrates an embodiment of a cart-based robotic system arranged for diagnostic and/or therapeutic bronchoscopy procedure(s).
Figure 2:
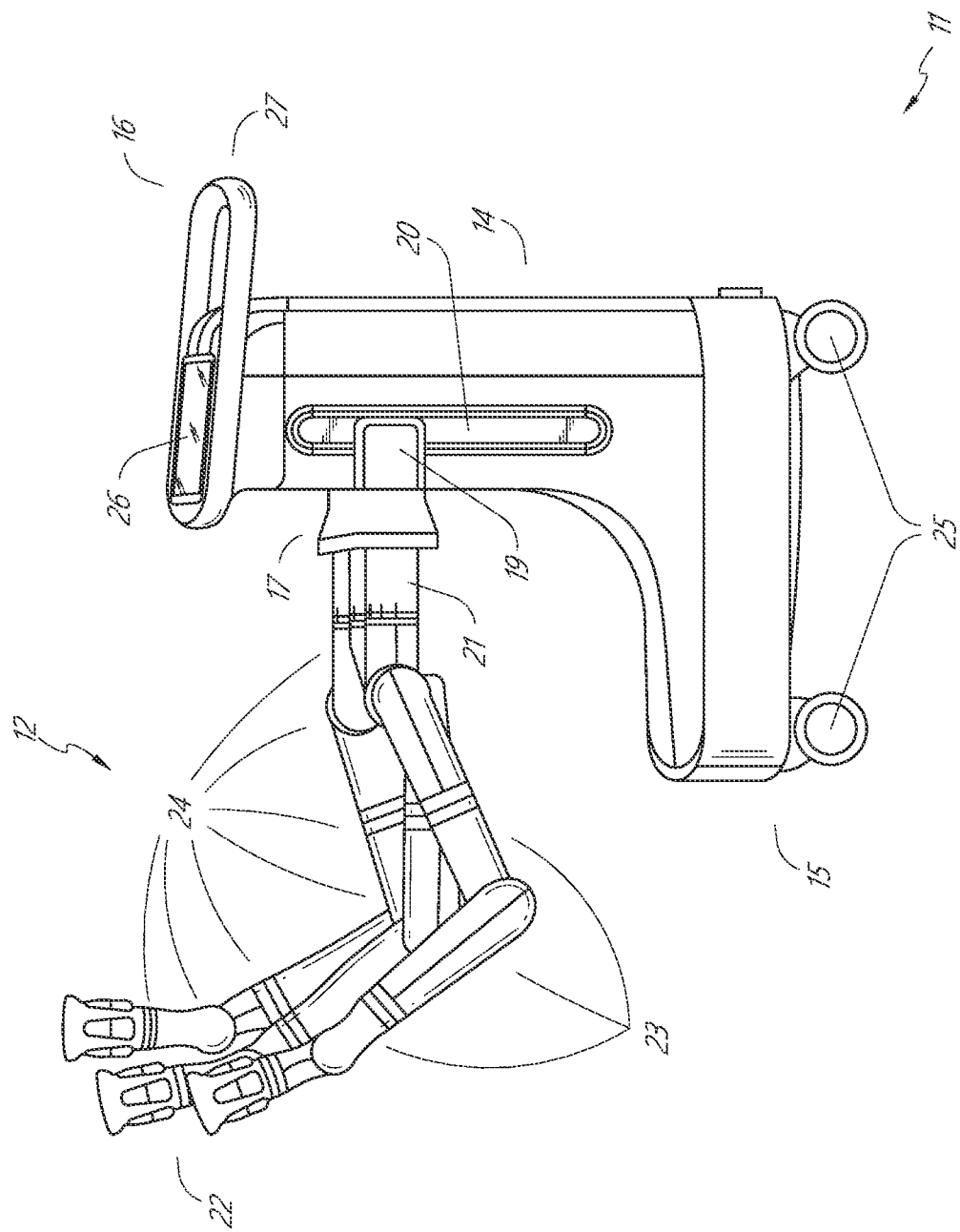
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
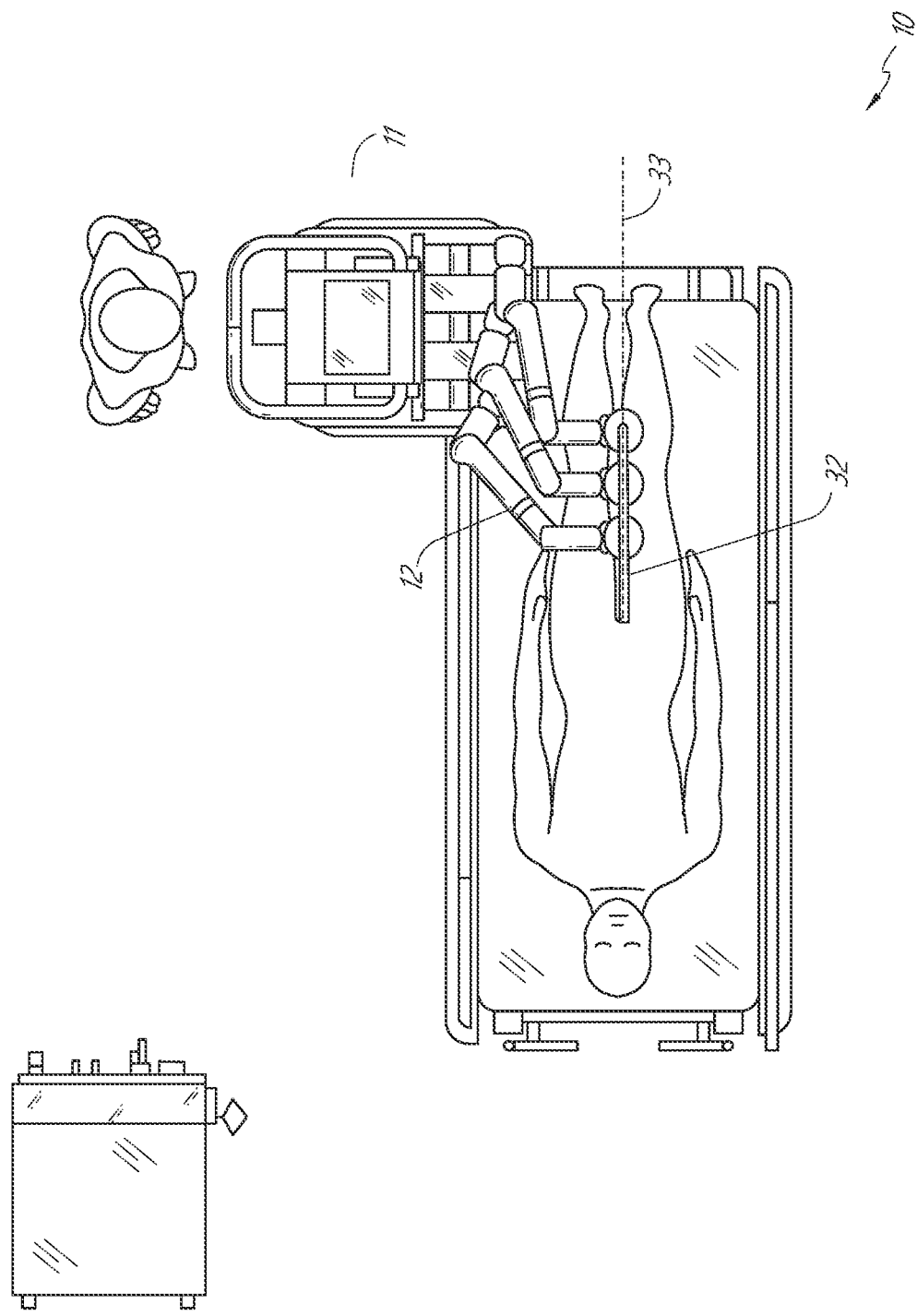
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
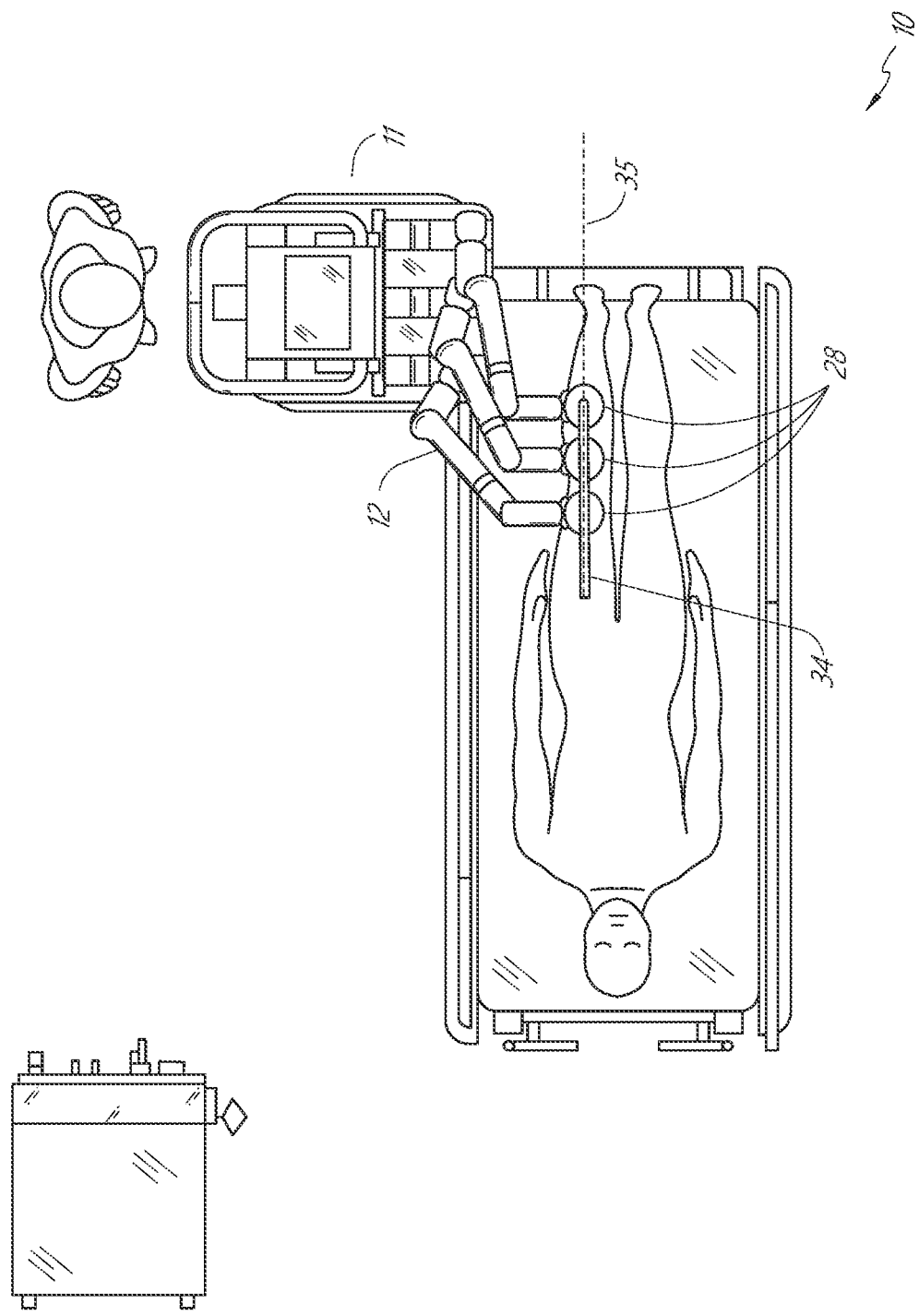
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
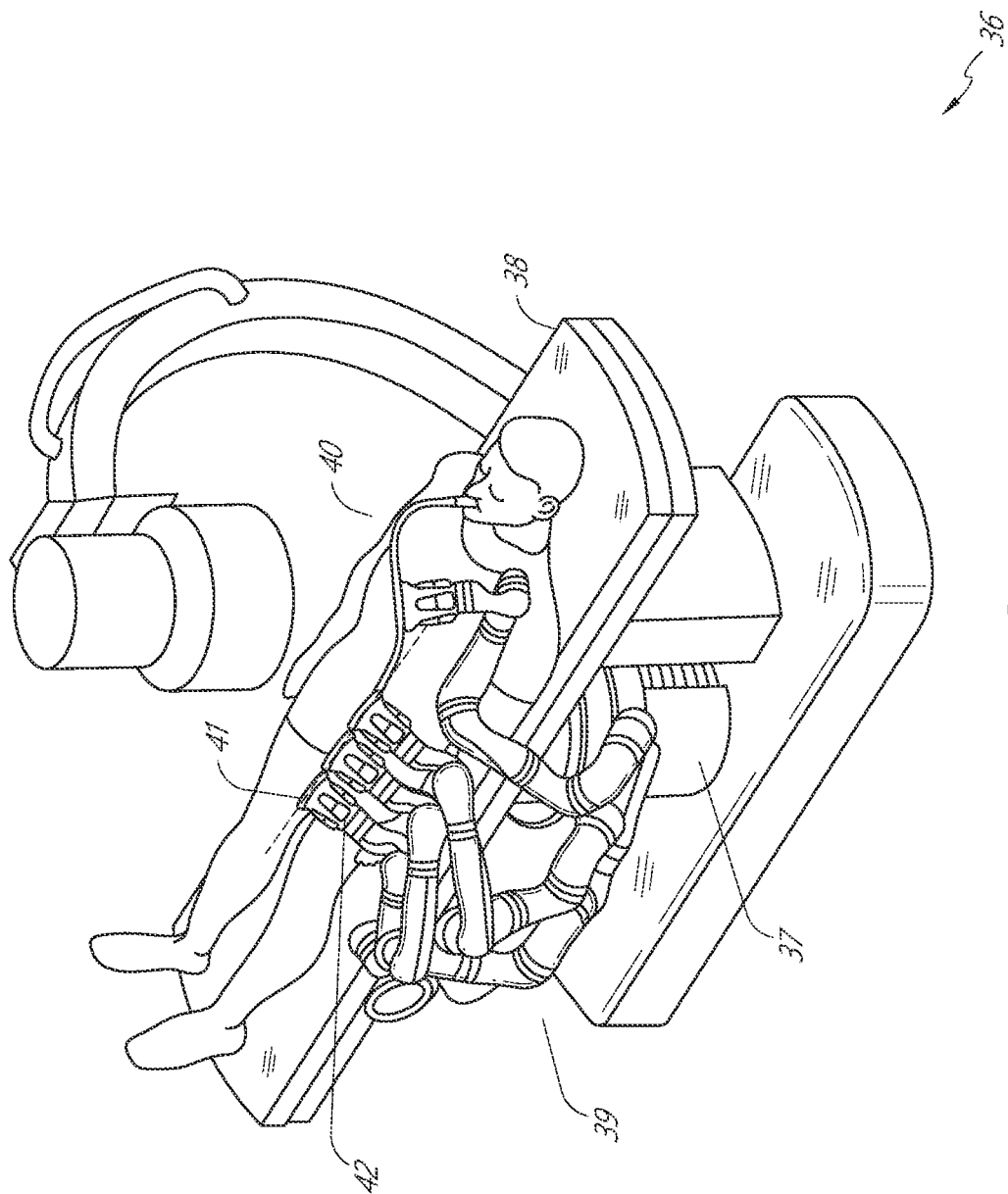
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
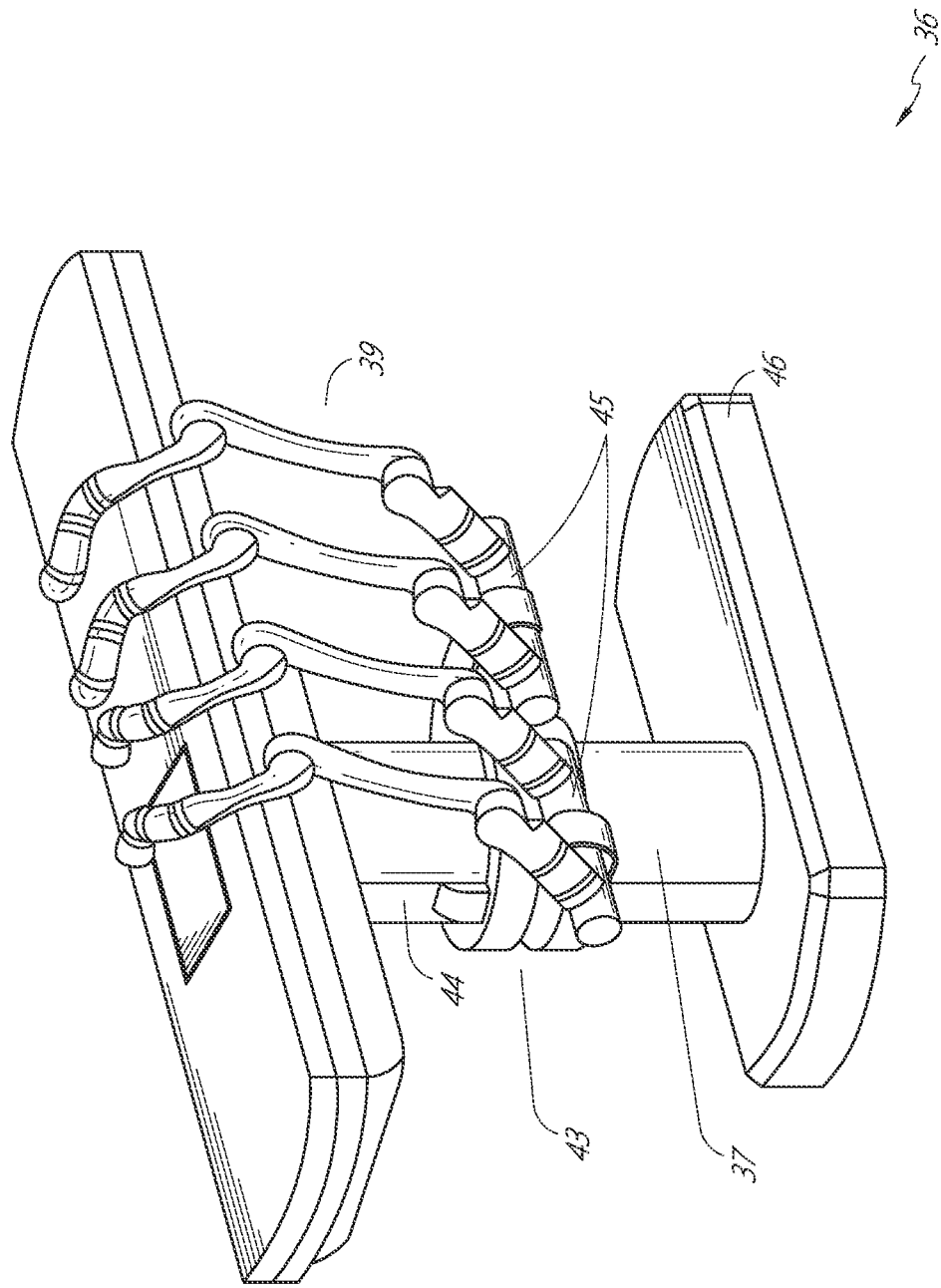
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
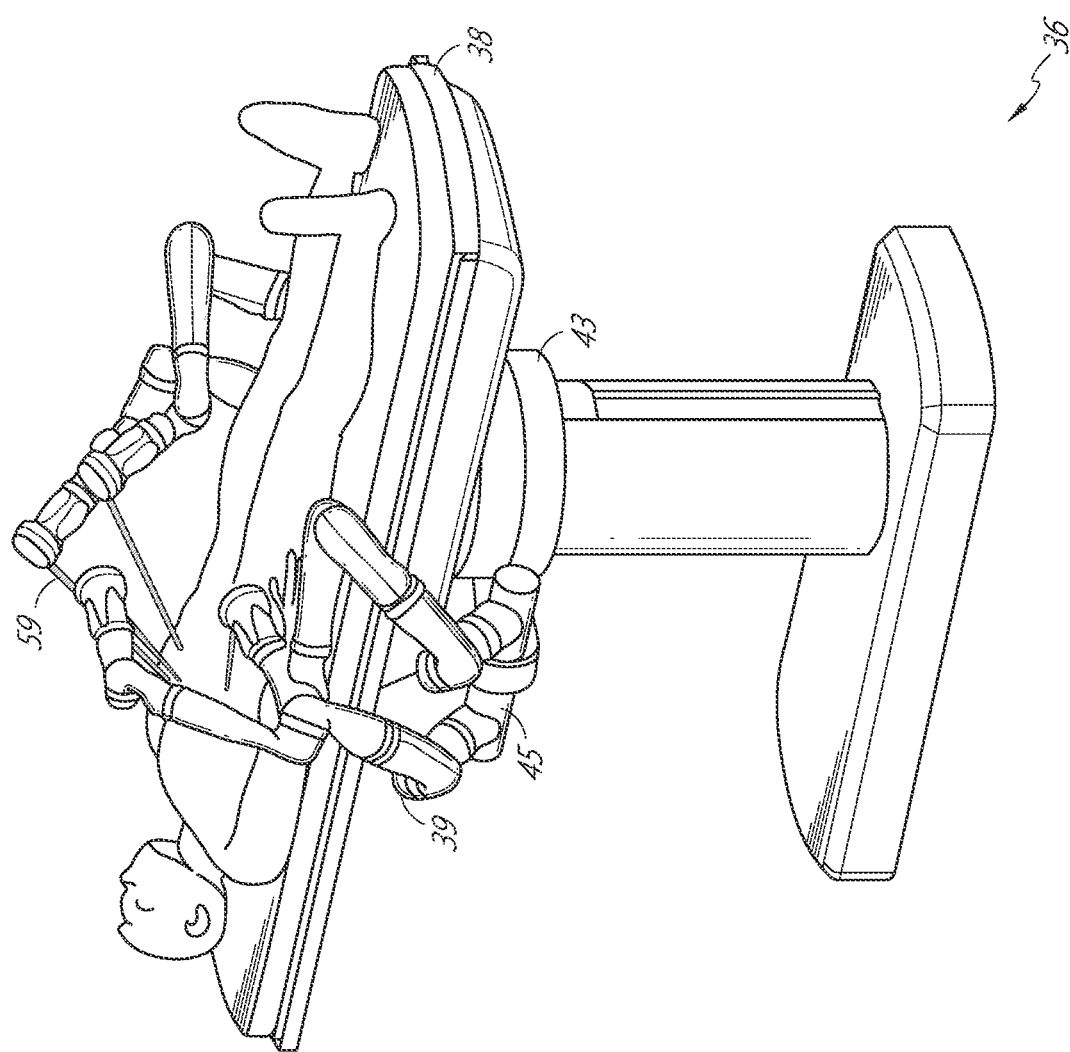
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
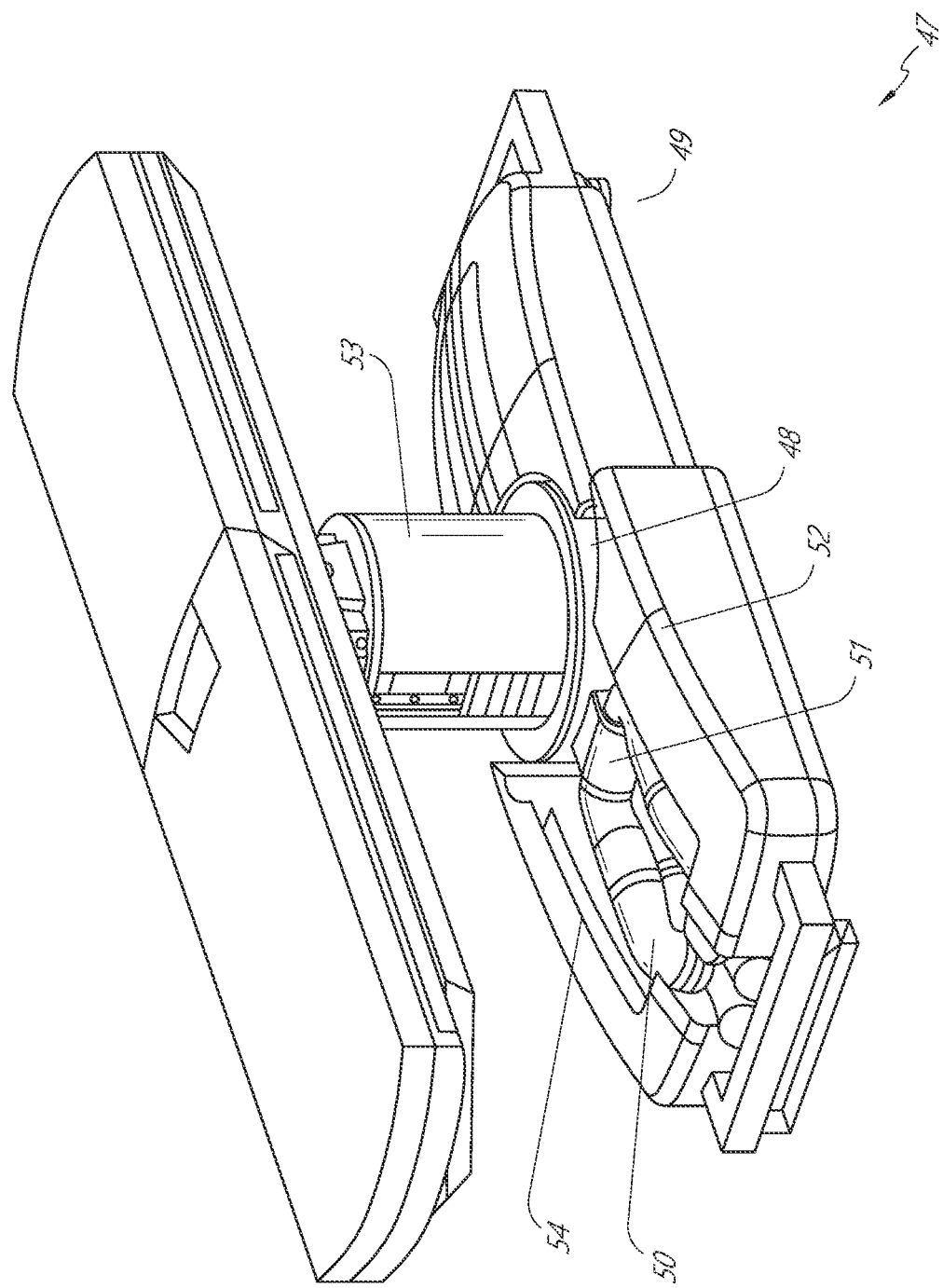
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
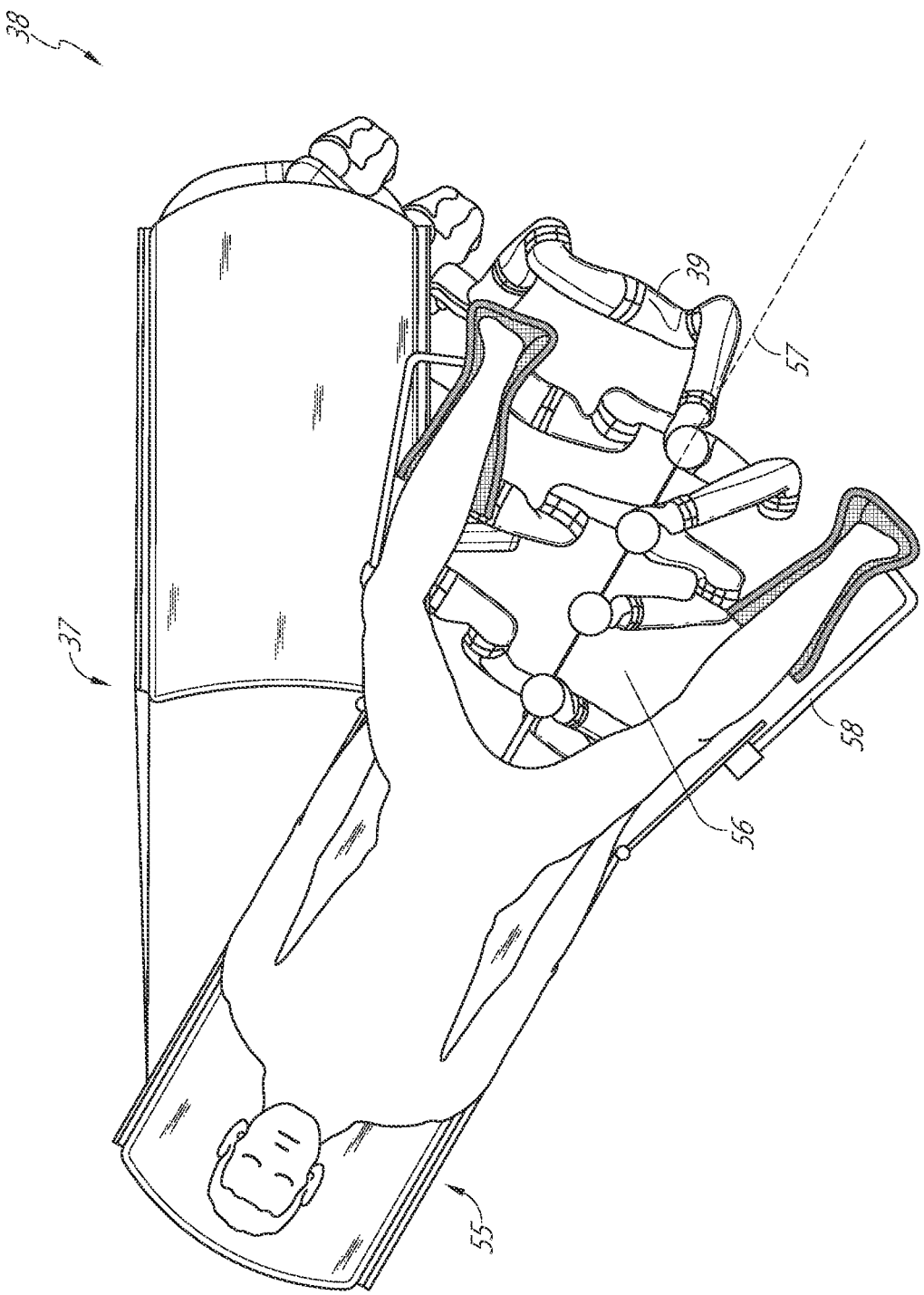
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
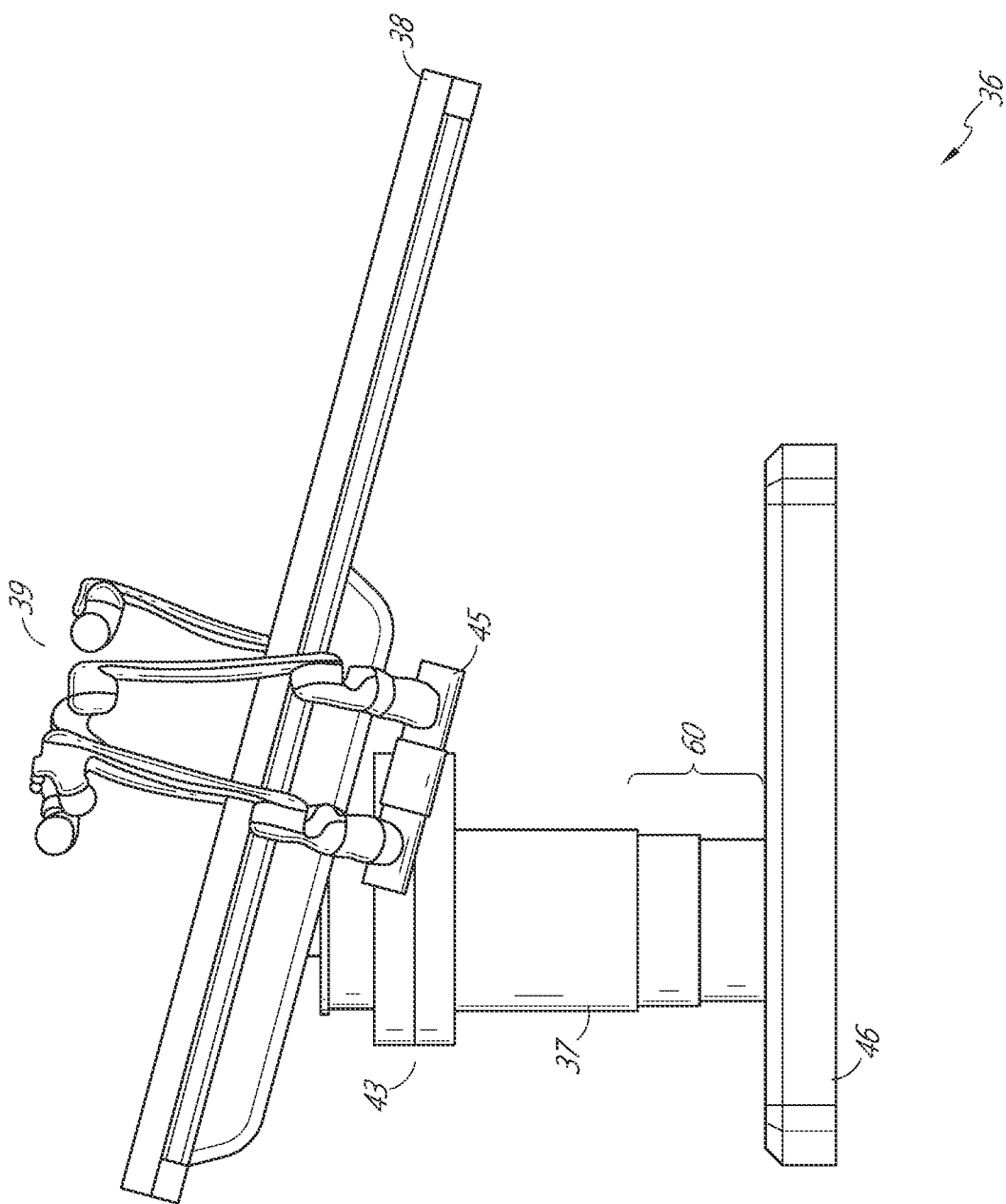
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
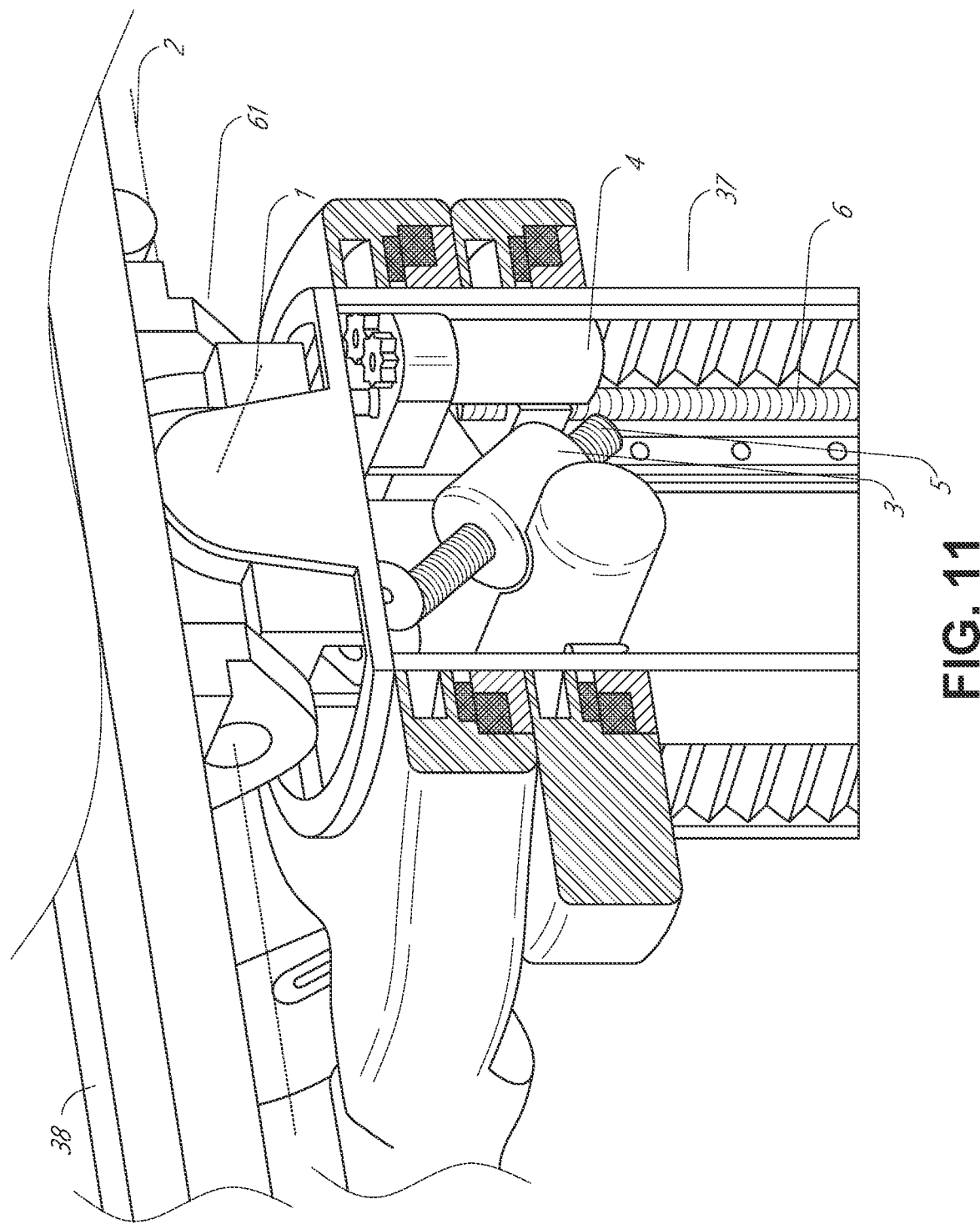
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
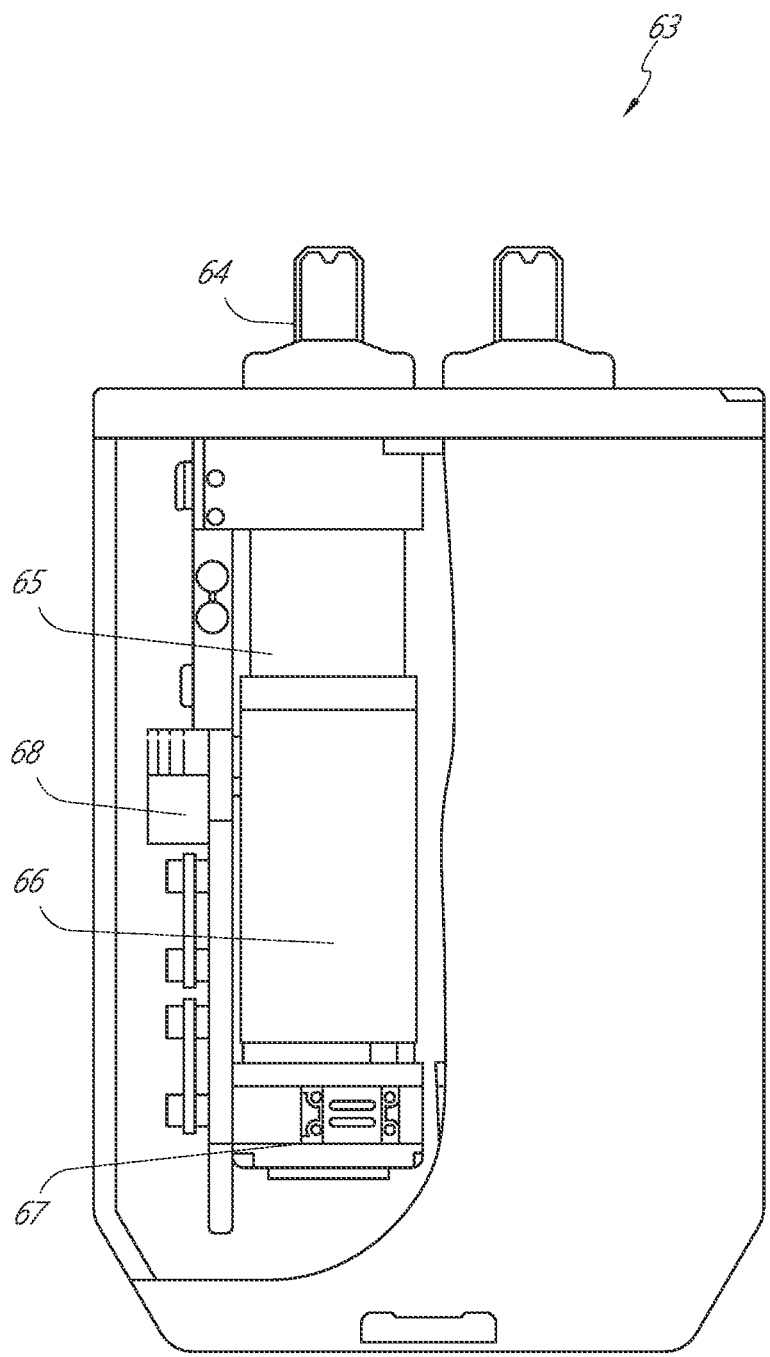
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
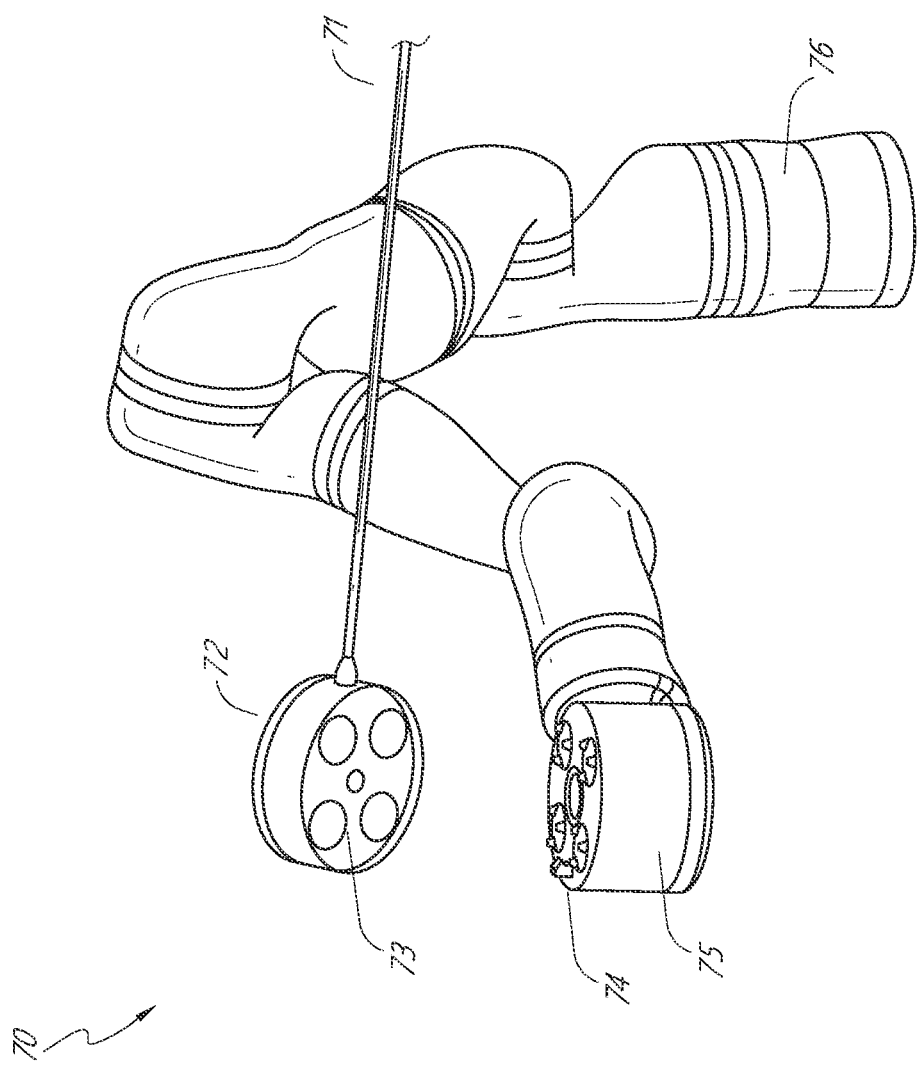
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
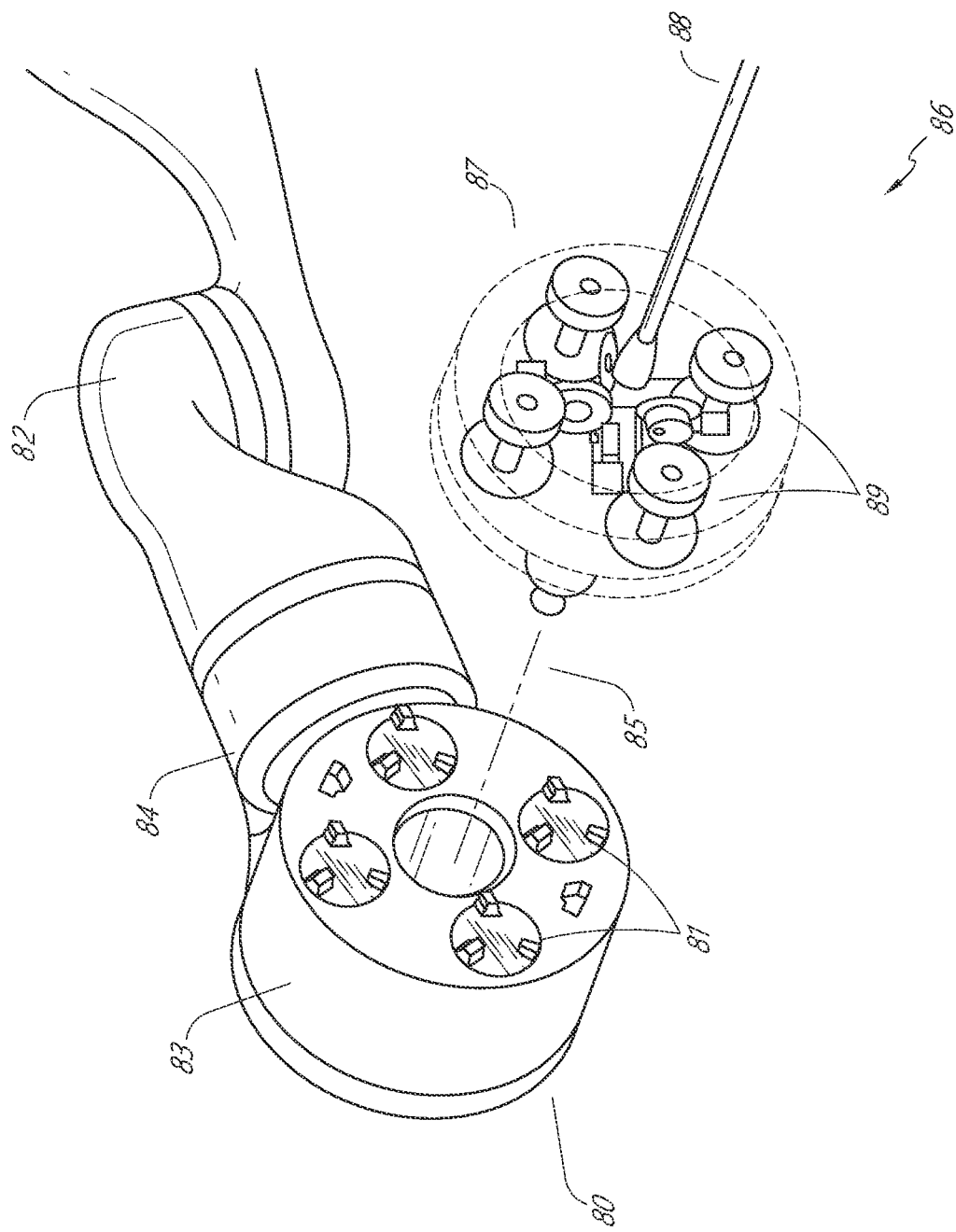
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator). The location data 96 may also be referred to herein as "state data" which describes a current state of the distal tip of the medical instrument with respect to a model (e.g., a skeletal model) of the anatomy of the patient. The state data may include information such as a position and orientation of the distal tip of the medical instrument for a given sample period. For example, when the patient's anatomy is modeled using a skeletal model based on a midpoint of the luminal network, the position may take the form of a segment ID and a depth along the segment.

The various input data 91-94 are now described in greater detail. Pre-operative mapping may be accomplished through the use of the collection of low dose CT scans. Pre-operative CT scans are reconstructed into three-dimensional (3D) images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a 3D volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing a shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Location Sensor-Based Branch Prediction

Embodiments of the disclosure relate to systems and techniques for location sensor-based branch prediction. The system may employ location sensor(s) or location sensing device(s) to localize the distal end of an instrument, for example, during a medical procedure. The location sensor(s) may be positioned at or near the distal end of the instrument or may be positioned remote from the distal end of the instrument. Examples of location sensors or location sensing devices which may be positioned at or near the distal end of the instrument include EM sensors, vision-based location sensors (e.g., a camera), shape sensing fibers, etc. Examples of location sensors or location sensing devices which may be positioned remotely from the distal end of the instrument include fluoroscopic imaging devices, robotic system component(s) that generate or process robotic data for controlling the position of the instrument via one or more instrument manipulators, remote vision-based location sensors, etc.

The location sensors may be configured to generate location data indicative of the location of the distal end of the instrument, for example, with respect to a location sensor coordinate system. As used herein, the location sensor coordinate system may refer to any coordinate system which can be used to define or determine the positions of the location data (e.g., on a manifold such as Euclidean space) generated by the location sensors. When the location sensors are collocated with the distal end of the instrument, the location data may be representative of the location of the location sensors themselves, which the processor can then use to determine the location of the distal end of the instrument. In certain embodiments, the location sensor coordinate system may comprise a set of axes and an origin, which may be defined based on the particular technology used to implement the location sensors.

For example, EM sensors located in or on the instrument may be configured to measure an EM field generated by an EM field generator. The properties of the EM field, and thus the EM values measured by the EM sensors, may be defined with respect to the location and orientation of the EM field generator. Thus, the positioning of the EM field generator may affect the values measured by the EM sensors and may also define the location and orientation of the EM coordinate system.

As described above, a luminal network of a patient may be pre-operatively mapped using, for example, low dose CT scans to produce a model of the luminal network. Since the model may be produced via a different technique than used to locate the distal end of the instrument, the model coordinate system may not be aligned with the location sensor coordinate system. Accordingly, in order to use the location sensor coordinate system to track the location of the instrument with respect to the model, one technique may involve registering (e.g., by one or more components of a robotic system or a separate system communicatively coupled to the robotic system, including but not limited to a processor, a localization system, a localization module, etc.) a coordinate system used by one or more location sensors with another coordinate system, such as a coordinate system used by an anatomical model. This registration may include, for example, translation and/or rotation applied to the location sensor data in order to map the location sensor data from the location sensor coordinate system into the model coordinate system.

The system or processor may perform registration of a location sensor coordinate system to the model coordinate system, for example, during an initial phase of the procedure. Depending on the implementation, the processor may perform the registration process automatically in the background as the instrument is initially advanced through the luminal network. In another implementation, the processor may provide a set of instructions to the user to drive the instrument to specific locations within the luminal network or along a set registration path to facilitation the registration process. Accordingly, the processor may perform a portion of the procedure while the location data received from the location sensor(s) is not registered to the model.

In order to provide feedback to the user regarding the navigation of the instrument during the medical procedure, a "fusion" localization algorithm may be run (e.g., by the localization system 90 of FIG. 15). The fusion algorithm may combine data indicative of the location of the distal end of the instrument received from a plurality of sources to determine the location of the instrument. One function of the fusion algorithm may also include the prediction of the next branch of the luminal network into which the instrument may be advanced. This prediction may be based on at least some of the data sources used in the fusion algorithm, including the location sensor data. In certain embodiments, the prediction may also be used as an input in the determination of the location of the distal end of the instrument.

Since the location sensor(s) may not be registered for at least a portion of the medical procedure, certain aspects of this disclosure may relate to techniques for branch prediction which may be employed based on registered location sensor data or unregistered location sensor data (also generally referred to as "raw" location sensor data). Thus, the system may selectively apply different techniques or combinations thereof for location sensor-based branch prediction depending on whether the location sensor(s) have been registered.

A. EM Navigation-Guided Bronchoscopy.

Hereinafter, an example system which may employ the techniques for location sensor-based branch prediction will be described. For example, the system may be configured for an EM navigation-guided bronchoscopic procedure. However, aspects of this disclosure may also apply to systems which use other location sensors which can produce location data as well as to other types of medical procedures.

Figure 16A:
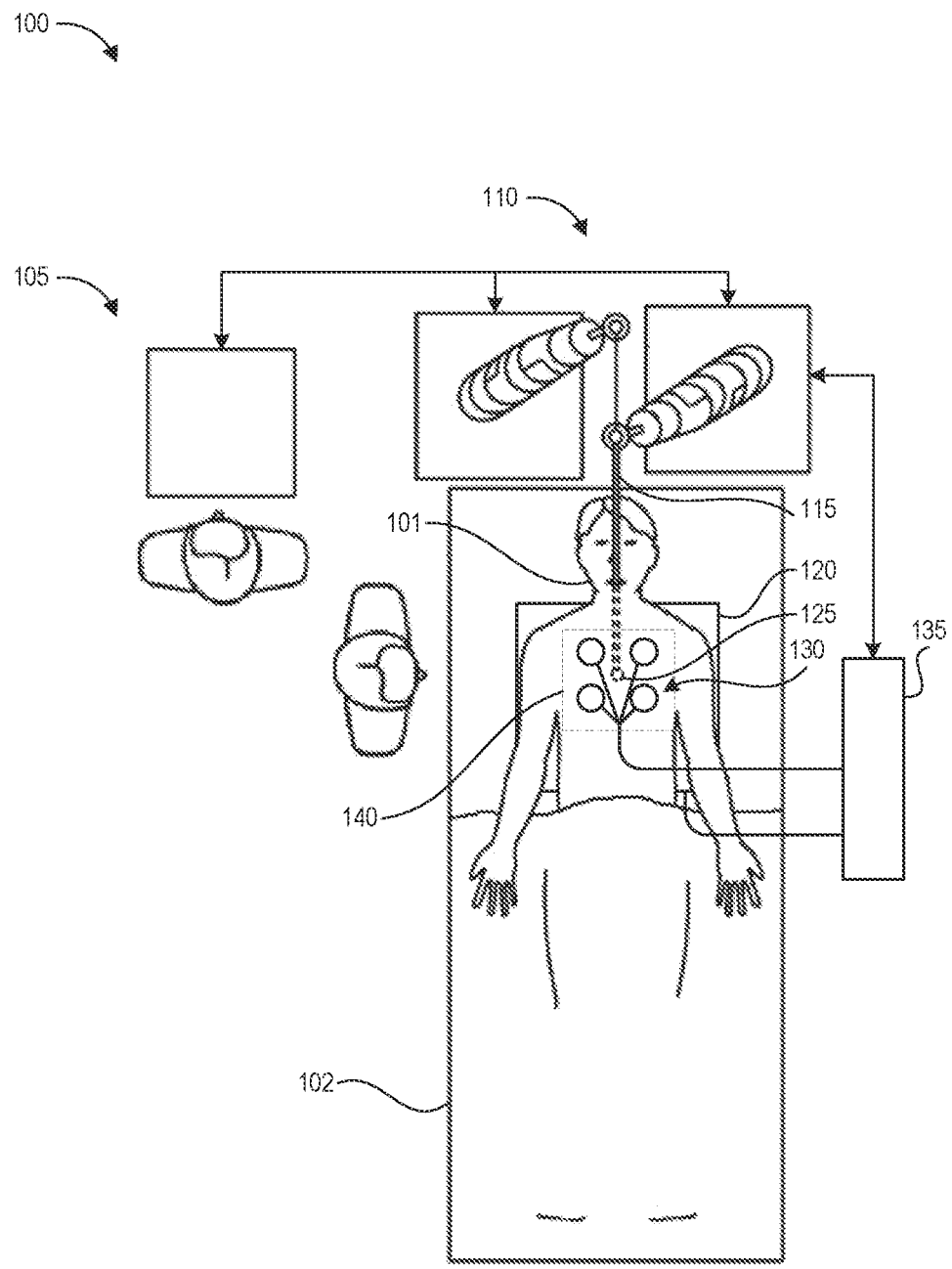
FIG. 16A illustrates an example operating environment implementing one or more aspects of the disclosed branch prediction systems and techniques.

FIG. 16A illustrates an example operating environment 100 which can implement one or more aspects of the disclosed branch prediction systems and techniques. The operating environment 100 can include a platform 102 supporting a patient 101, a surgical or medical robotic system 110 guiding movement of an instrument 115, a command center 105 for controlling operations of the robotic system 110, EM controller 135, EM field generator 120, and EM sensors 125, 130. FIG. 16A also illustrates an outline of a region of a luminal network 140 within the patient 101, shown in more detail in FIG. 16B.

The system 110 can include one or more robotic arms for positioning and guiding movement of the instrument 115 through the luminal network 140 of the patient 101. The command center 105 can be communicatively coupled to the robotic system 110 for receiving position data and/or providing control signals generated based on user commands received from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The robotic system 110 can be any of the systems described above with respect to FIGS. 1-15.

The instrument 115 may be a tubular and flexible surgical instrument that is inserted into the anatomy of a patient to capture images of the anatomy (e.g., body tissue) and provide a working channel for insertion of other medical instruments to a target tissue site. As described above, the instrument 115 can be a procedure-specific endoscope, for example a bronchoscope, gastroscope, or ureteroscope, or may be a laparoscope or vascular steerable catheter. The instrument 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the instrument 115 such that movement of the tip of the instrument 115 results in corresponding changes to the field of view of the images captured by the imaging devices. The distal end of the instrument 115 can be provided with one or more EM sensors 125 for tracking the position of the distal end within an EM field generated around the luminal network 140.

The EM controller 135 can control the EM field generator 120 to produce a varying EM field. The EM field can be time-varying and/or spatially varying, depending upon the embodiment. The EM field generator 120 can be an EM field generating board in some embodiments. Some embodiments of the disclosed systems can use an EM field generator board positioned between the patient and the platform 102 supporting the patient 101, and the EM field generator board can incorporate a thin barrier that minimizes tracking distortions caused by conductive or magnetic materials located below it. In other embodiments, an EM field generator board can be mounted on a robotic arm, for example, similar to those shown in the robotic system 110, which can offer flexible setup options around the patient.

Figure 16B:
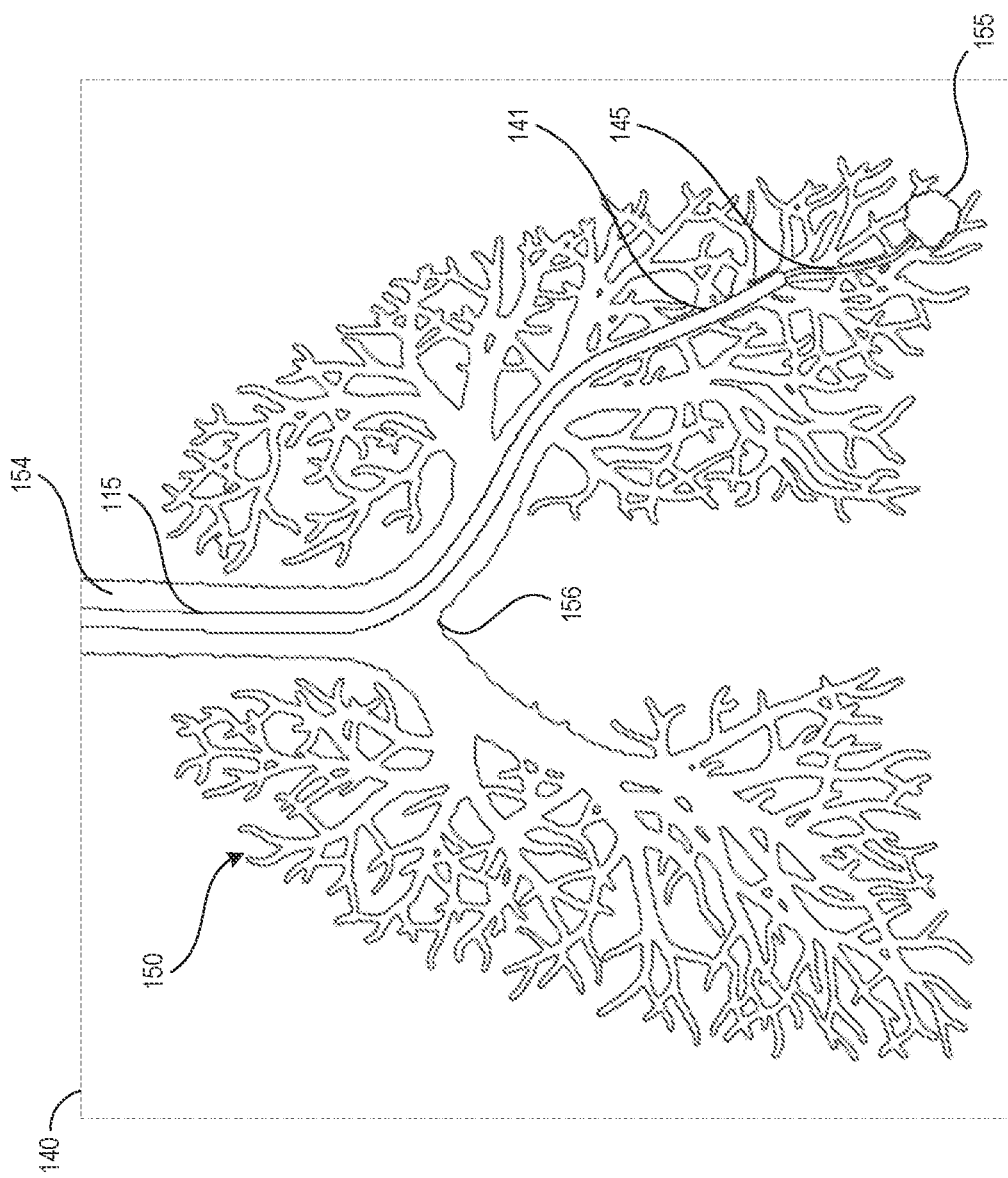
FIG. 16B illustrates an example luminal network that can be navigated in the operating environment of FIG. 16A.

FIG. 16B illustrates an example luminal network 140 that can be navigated in the operating environment 100 of FIG. 16A. The luminal network 140 includes the branched structure of the airways 150 of the patient 101, the trachea 154 leading to the main carina 156 (typically the first bifurcation encountered during bronchoscopy navigation), and a nodule (or lesion) 155 that can be accessed as described herein for diagnosis and/or treatment. As illustrated, the nodule 155 is located at the periphery of the airways 150. The instrument 115 may comprise a sheath 141 having a first diameter and thus the distal end of the sheath 141 may not able to be positioned through the smaller-diameter airways around the nodule 155. Accordingly, a scope 145 extends from the working channel of the instrument 115 and across the remaining distance to the nodule 155. The scope 145 may have a lumen through which instruments, for example, biopsy needles, cytology brushes, and/or tissue sampling forceps, can be passed to the target tissue site of nodule 155. In such implementations, both the distal end of the sheath 141 and the distal end of the scope 145 can be provided with EM sensors for tracking their respective positions within the airways 150.

In some embodiments, a two-dimensional (2D) display of a 3D luminal network model as described herein, or a cross-section of the 3D model, can resemble FIG. 16B. An estimated location of the distal end of the instrument can be overlaid onto such a representation. In certain implementations, the estimated location may be displayed on a display of a command console, such as the command console 160 illustrated in FIG. 16C.

Figure 16C:
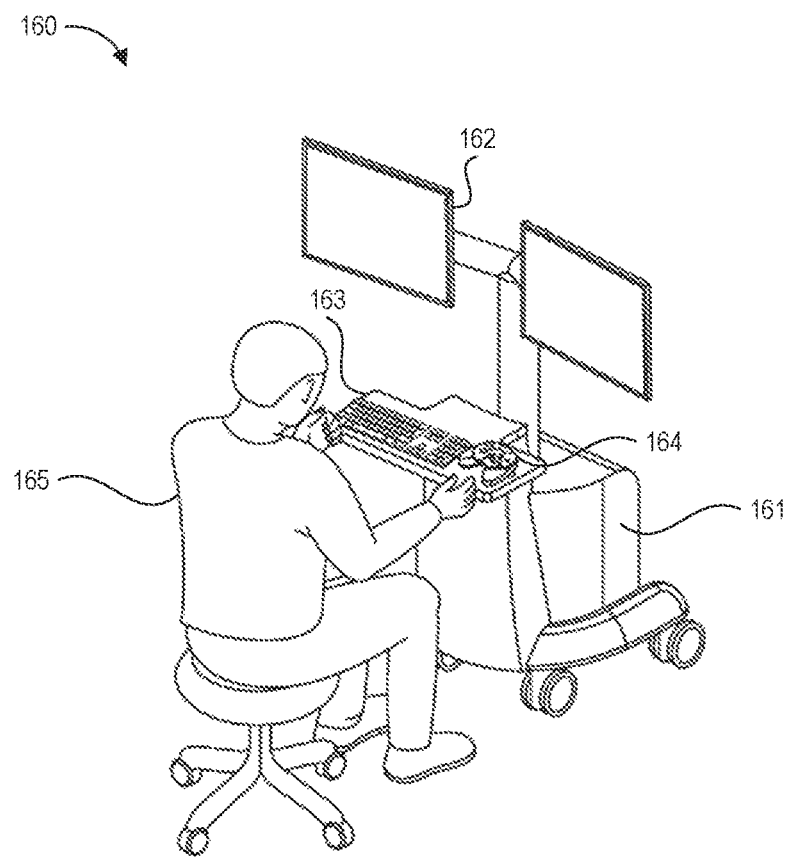
FIG. 16C illustrates an example command console that can be used, for example, as the command console in the example operating environment.

FIG. 16C illustrates an example command console 160 that can be used, for example, as the command console 105 in the example operating environment 100. The command console 160 may include a console base 161, one or more display 162 (e.g., monitors), and one or more control modules (e.g., a keyboard 163 and joystick 164). In some embodiments, one or more of the command console 160 functionality may be integrated into a base 180 of the robotic system 110 or another system communicatively coupled to the robotic system 110. A user 165, e.g., a physician, remotely controls the robotic system 110 from an ergonomic position using the command console 160.

The console base 161 may include a central processing unit, a memory unit, a data bus, and associated data communication ports that are responsible for interpreting and processing signals such as camera imagery and tracking sensor data, e.g., from the instrument 115 shown in FIGS. 16A and 16B. In some embodiments, both the console base 161 and the base 180 perform signal processing for load-balancing. The console base 161 may also process commands and instructions provided by the user 165 through the control modules 163 and 164. In addition to the keyboard 163 and joystick 164 shown in FIG. 16C, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped or linked to an operation of the instrument (e.g., articulation, driving, water irrigation, etc.).

The displays 162 may include electronic monitors (e.g., LCD displays, LED displays, touch-sensitive displays), virtual reality viewing devices, e.g., goggles or glasses, and/or other display devices. In some embodiments, the display modules 162 are integrated with the control modules, for example, as a tablet device with a touchscreen. In some embodiments, one of the displays 162 can display a 3D model of the patient's luminal network and virtual navigation information (e.g., a virtual representation of the end of the endoscope within the model based on EM sensor position) while the other of the displays 162 can display image information received from the camera or another sensing device at the end of the instrument 115. In some implementations, the user 165 can both view data and input commands to the system 110 using the integrated displays 162 and control modules. The displays 162 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an instrument 115 inside the patient. A user 165 compares the "endo view" model to actual images captured by a camera to help mentally orient and confirm that the instrument 115 is in the correct—or approximately correct—location within the patient. The "endo view" provides information about anatomical structures, e.g., the shape of airways, circulatory vessels, or an intestine or colon of the patient, around the distal end of the instrument 115. The display modules 162 can simultaneously display the 3D model and CT scans of the anatomy the around distal end of the instrument 115. Further, the display modules 162 may overlay the already determined navigation paths of the instrument 115 on the 3D model and CT scans.

In some embodiments, a model of the instrument 115 is displayed with the 3D models to help indicate a status of a surgical procedure. For example, the CT scans identify a lesion in the anatomy where a biopsy may be necessary. During operation, the display modules 162 may show a reference image captured by the instrument 115 corresponding to the current location of the instrument 115. The display modules 162 may automatically display different views of the model of the instrument 115 depending on user settings and a particular surgical procedure. For example, the display modules 162 show an overhead fluoroscopic view of the instrument 115 during a navigation step as the instrument 115 approaches an operative region of a patient.

B. Location Sensor-Based Branch Prediction Using Unregistered Location Data.

As discussed above, an initial phase of a medical procedure may be performed before the location sensor(s) are registered to a model of the luminal network. However, the location sensor(s) may still produce location data prior to registration. Although unregistered to the model, the raw location sensor data may be useful to provide certain localization and navigational functionality. For example, the processor can determine the relative orientations of the instrument at different times based on the raw, unregistered location data. Thus, in certain embodiments, based on the shape and structure of the luminal network and the orientation of the instrument determined based on the unregistered data, the processor may facilitate predicting the next branch of the luminal network into which the instrument is likely to be advanced.

Figure 17A:
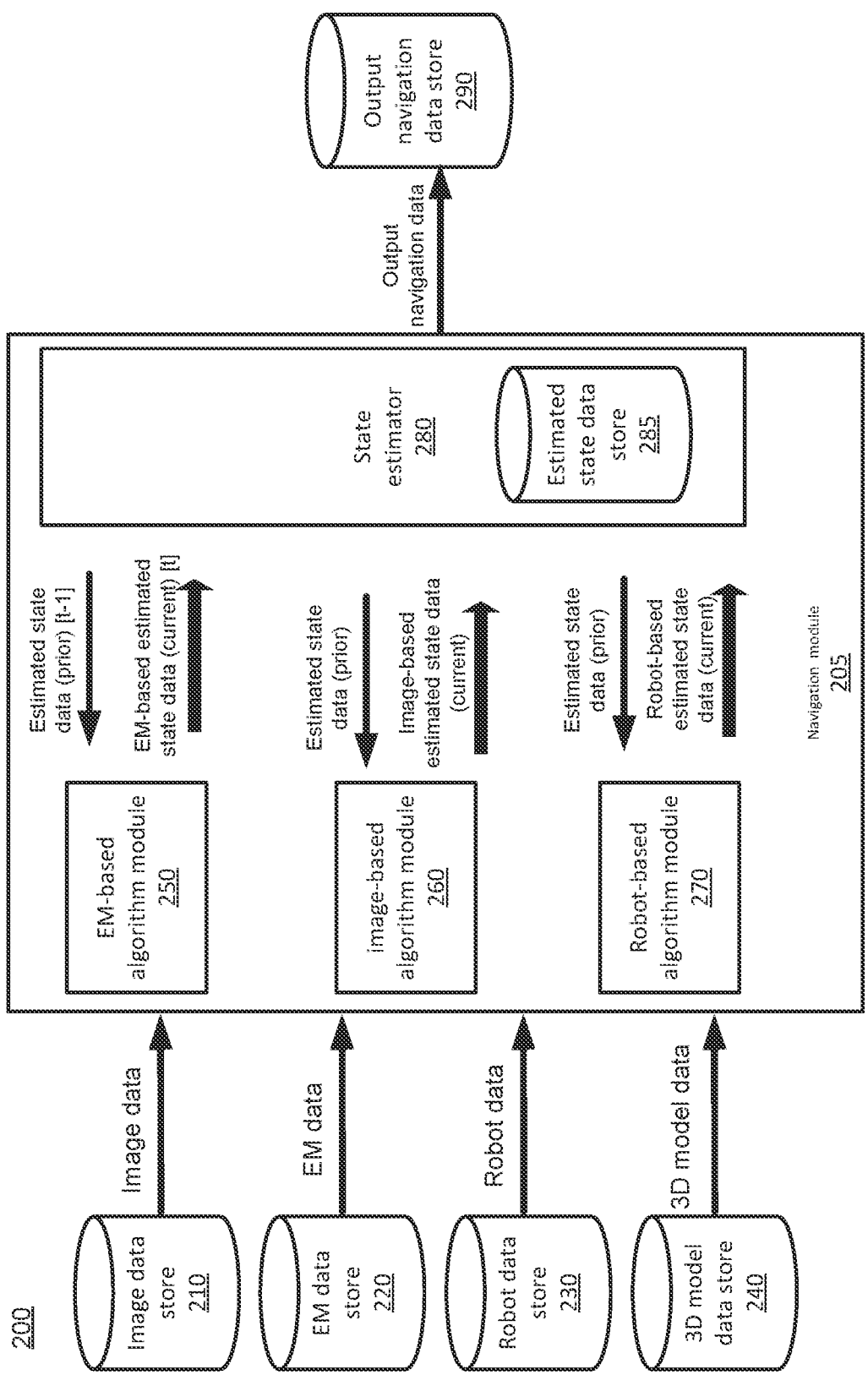
FIG. 17A provides an overview of an example block diagram of the navigation configuration system, according to one embodiment.

Branch prediction may be included as part of a navigation configuration system. FIGS. 17A-17D show example block diagrams of a navigation configuration system 200, according to one embodiment. More specifically, FIG. 17A provides an overview of an example block diagram of the navigation configuration system 200, according to one embodiment. In FIG. 17A, the navigation configuration system 200 includes multiple input data stores, a navigation module 205 that receives various types of input data from the multiple input data stores, and an output navigation data store 290 that receives output navigation data from the navigation module. The block diagram of the navigation configuration system 200 shown in FIG. 17A is merely one example, and in alternative embodiments not shown, the navigation configuration system 200 can include different and/or addition entities. Likewise, functions performed by various entities of the system 200 may differ according to different embodiments. The navigation configuration system 200 may be similar to the navigational system described in U.S. Patent Publication No. 2017/0084027, published on Mar. 23, 2017, the entirety of which is incorporated herein by reference.

The input data, as used herein, refers to raw data gathered from and/or processed by input devices (e.g., command module(s), optical sensor(s), EM sensor(s), IDM(s)) for generating estimated state information for the endo scope as well as output navigation data. The multiple input data stores 210-240 include an image data store 210, an EM data store 220, a robot data store 230, and a 3D model data store 240. Each type of the input data stores 210-240 stores the name-indicated type of data for access and use by a navigation module 205. Image data may include one or more image frames captured by the imaging device at the instrument tip, as well as information such as frame rates or timestamps that allow a determination of the time elapsed between pairs of frames. Robot data may include data related to physical movement of the medical instrument or part of the medical instrument (e.g., the instrument tip or sheath) within the tubular network. Example robot data includes command data instructing the instrument tip to reach a specific anatomical site and/or change its orientation (e.g., with a specific pitch, roll, yaw, insertion, and retraction for one or both of a leader and a sheath) within the tubular network, insertion data representing insertion movement of the part of the medical instrument (e.g., the instrument tip or sheath), IDM data, and mechanical data representing mechanical movement of an elongate member of the medical instrument, for example motion of one or more pull wires, tendons or shafts of the endoscope that drive the actual movement of the medial instrument within the tubular network. EM data may be collected by EM sensors and/or the EM tracking system as described above. 3D model data may be derived from 2D CT scans as described above. Path data includes the planned navigation path which may be generated by a topological search of the tubular network to one or more targets.

The output navigation data store 290 receives and stores output navigation data provided by the navigation module 205. Output navigation data indicates information to assist in directing the medical instrument through the tubular network to arrive at a particular destination within the tubular network, and is based on estimated state information for the medical instrument at each instant time, the estimated state information including the location and orientation of the medical instrument within the tubular network. In one embodiment, as the medical instrument moves inside the tubular network, the output navigation data indicating updates of movement and location/orientation information of the medical instrument is provided in real time, which better assists its navigation through the tubular network.

To determine the output navigation data, the navigation module 205 locates (or determines) the estimated state of the medical instrument within a tubular network. As shown in FIG. 17A, the navigation module 205 further includes various algorithm modules, such as an EM-based algorithm module 250, an image-based algorithm module 260, and a robot-based algorithm module 270, that each may consume mainly certain types of input data and contribute a different type of data to a state estimator 280. As illustrated in FIG. 17A, the different kinds of data output by these modules, labeled EM-based data, the image-based data, the robot-based data, and the path-based data, may be generally referred to as "intermediate data" for sake of explanation.

Figure 17B:
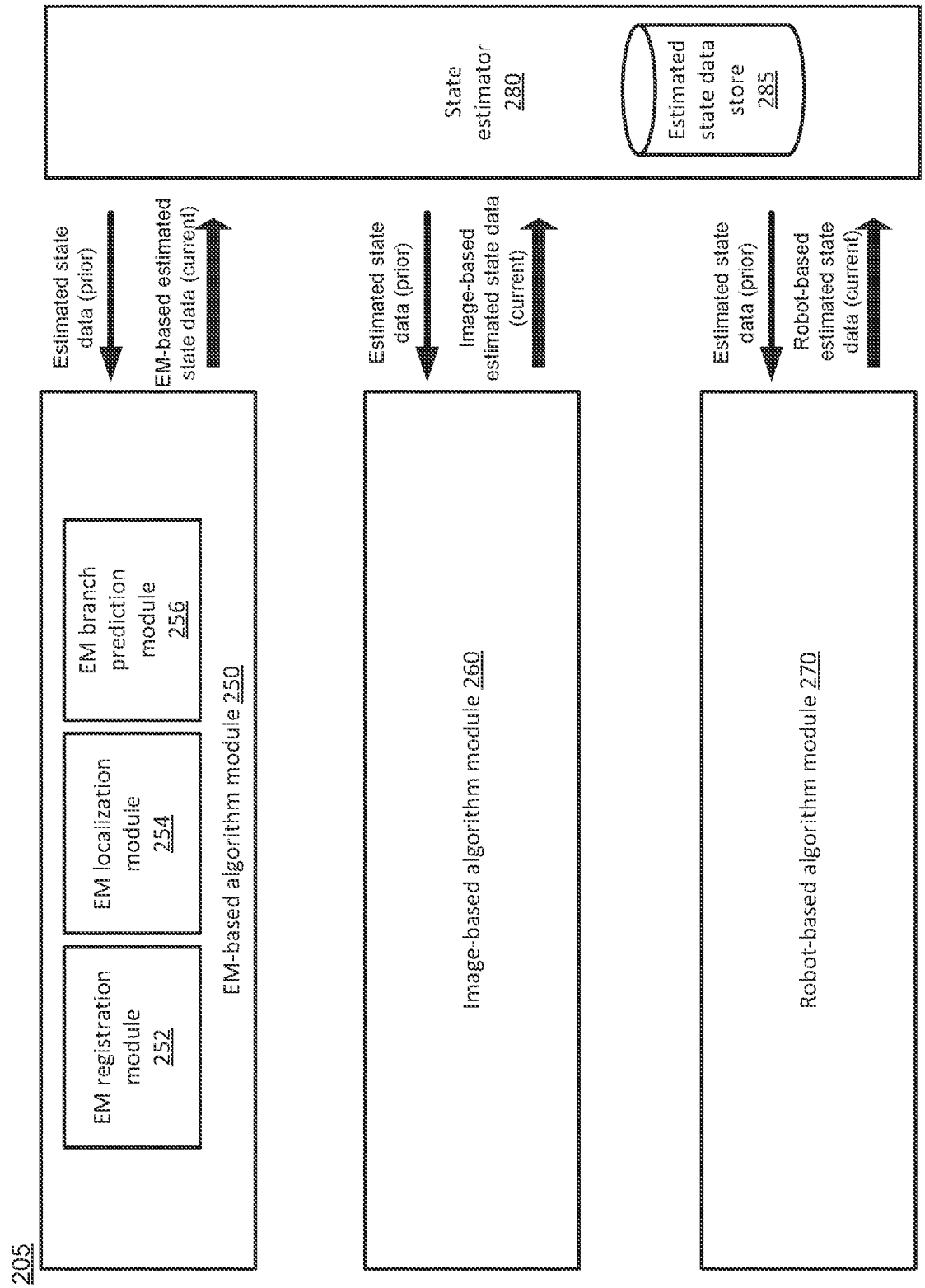
FIG. 17B shows an example block diagram of the navigation module shown in FIG. 17A, according to one embodiment.

FIG. 17B shows an example block diagram of the navigation module 205 shown in FIG. 17A, according to one embodiment. As introduced above, the navigation module 205 further includes a state estimator 280 as well as multiple algorithm modules that employ different algorithms for navigating through a tubular network. For clarity of description, the state estimator 280 is described first, followed by the description of the various modules that exchange data with the state estimator 280.

The state estimator 280 included in the navigation module 205 receives various intermediate data and provides the estimated state of the instrument tip as a function of time, where the estimated state indicates the estimated location and orientation information of the instrument tip within the tubular network. The estimated state data are stored in the estimated data store 285 that is included in the state estimator 280.

Figure 17C:
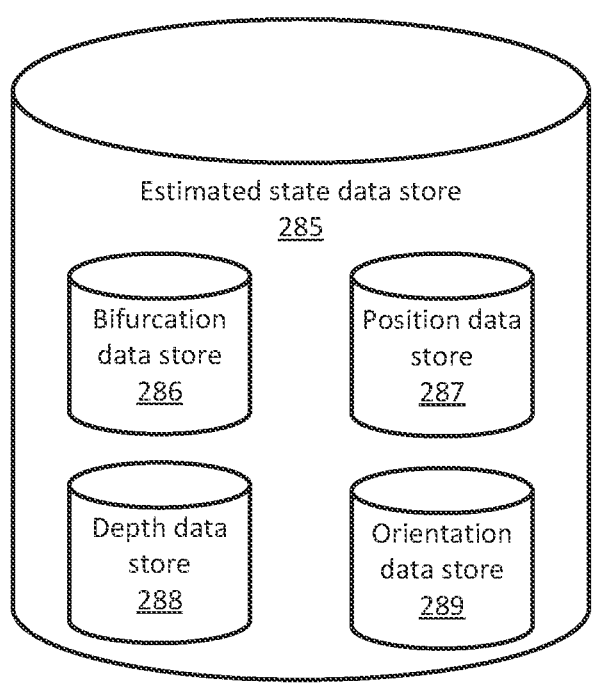
FIG. 17C shows an example block diagram of the estimated state data store included in the state estimator, according to one embodiment.

FIG. 17C shows an example block diagram of the estimated state data store 285 included in the state estimator 280, according to one embodiment. The estimated state data store 285 may include a bifurcation data store 286, a position data store 287, a depth data store 288, and an orientation data store 289, however this particular breakdown of data storage is merely one example, and in alternative embodiments not shown, different and/or additional data stores can be included in the estimated state data store 285.

The various stores introduced above represent estimated state data in a variety of ways. Specifically, bifurcation data refers to the location of the medical instrument with respect to the set of branches (e.g., bifurcation, trifurcation or a division into more than three branches) within the tubular network. For example, the bifurcation data can be set of branch choices elected by the instrument as it traverses through the tubular network, based on a larger set of available branches as provided, for example, by the 3D model which maps the entirety of the tubular network. The bifurcation data can further include information in front of the location of the instrument tip, such as branches (bifurcations) that the instrument tip is near but has not yet traversed through, but which may have been detected, for example, based on the tip's current position information relative to the 3D model, or based on images captured of the upcoming bifurcations.

Position data indicates three-dimensional position of some part of the medical instrument within the tubular network or some part of the tubular network itself. Position data can be in the form of absolute locations or relative locations relative to, for example, the 3D model of the tubular network. As one example, position data can include an indication of the position of the location of the instrument being within a specific branch. The identification of the specific branch may also be stored as a segment identification (ID) which uniquely identifies the specific segment of the model in which the instrument tip is located.

Depth data indicates depth information of the instrument tip within the tubular network. Example depth data includes the total insertion (absolute) depth of the medical instrument into the patient as well as the (relative) depth within an identified branch (e.g., the segment identified by the position data store 287). Depth data may be determined based on position data regarding both the tubular network and medical instrument.

Orientation data indicates orientation information of the instrument tip, and may include overall roll, pitch, and yaw in relation to the 3D model as well as pitch, roll, raw within an identified branch.

Turning back to FIG. 17B, the state estimator 280 provides the estimated state data back to the algorithm modules for generating more accurate intermediate data, which the state estimator uses to generate improved and/or updated estimated states, and so on forming a feedback loop. For example, as shown in FIG. 17B, the EM-based algorithm module 250 receives prior EM-based estimated state data, also referred to as data associated with timestamp "t-1." The state estimator 280 uses this data to generate "estimated state data (prior)" that is associated with timestamp "t-1." The state estimator 280 then provides the data back to the EM-based algorithm module. The "estimated state data (prior)" may be based on a combination of different types of intermediate data (e.g., robotic data, image data) that is associated with timestamp "t-1" as generated and received from different algorithm modules. Next, the EM-based algorithm module 250 runs its algorithms using the estimated state data (prior) to output to the state estimator 280 improved and updated EM-based estimated state data, which is represented by "EM-based estimated state data (current)" here and associated with timestamp t. This process continues to repeat for future timestamps as well.

As the state estimator 280 may use several different kinds of intermediate data to arrive at its estimates of the state of the medical instrument within the tubular network, the state estimator 280 is configured to account for the various different kinds of errors and uncertainty in both measurement and analysis that each type of underlying data (robotic, EM, image, path) and each type of algorithm module might create or carry through into the intermediate data used for consideration in determining the estimated state. To address these, two concepts are discussed, that of a probability distribution and that of confidence value.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the tubular network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution. Different methods or modalities can be used to generate the probabilities, which will vary by algorithm module as more fully described below with reference to later figures.

In contrast, the "confidence value," as used herein, reflects a measure of confidence in the estimation of the state provided by one of the algorithms based one or more factors. For the EM-based algorithms, factors such as distortion to EM Field, inaccuracy in EM registration, shift or movement of the patient, and respiration of the patient may affect the confidence in estimation of the state. Particularly, the confidence value in estimation of the state provided by the EM-based algorithms may depend on the particular respiration cycle of the patient, movement of the patient or the EM field generators, and the location within the anatomy where the instrument tip locates. For the image-based algorithms, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM}*P_{1,EM} + C_{Image}*P_{1,Image} + C_{Robot}*P_{1,Robot};$$

$$S_2 = C_{EM}*P_{2,EM} + C_{Image}*P_{2,Image} + C_{Robot}*P_{2,Robot};$$

$$S_3 = C_{EM}*P_{3,EM} + C_{Image}*P_{3,Image} + C_{Robot}*P_{3,Robot}.$$

In the example mathematical equation above, $S_i (i=1, 2, 3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represent the probabilities for segment i.

To better illustrate the concepts of probability distributions and confidence value associated with estimate states, a detailed example is provided here. In this example, a user is trying to identify segment where an instrument tip is located in a certain trifurcation within a central airway (the predicted region) of the tubular network, and three algorithms modules are used including EM-based algorithm, image-based algorithm, and robot-based algorithm. In this example, a probability distribution corresponding to the EM-based algorithm may be 20% in the first branch, 30% in the second branch, and 50% in the third (last) branch, and the confidence value applied to this EM-based algorithm and the central airway is 80%. For the same example, a probability distribution corresponding to the image-based algorithm may be 40%, 20%, 40% for the first, second, and third branch, and the confidence value applied to this image-based algorithm is 30%; while a probability distribution corresponding to the robot-based algorithm may be 10%, 60%, 30% for the first, second, and third branch, and the confidence value applied to this image-based algorithm is 20%. The difference of confidence values applied to the EM-based algorithm and the image-based algorithm indicates that the EM-based algorithm may be a better choice for segment identification in the central airway, compared with the image-based algorithm. An example mathematical calculation of a final estimated state can be:

for the first branch: 20%*80%+40%*30%+10%*20%=30%; for the second branch: 30%*80%+20%*30%+60%*20%=42%; and for the third branch: 50%*80%+40%*30%+30%*20%=58%.

In this example, the output estimated state for the instrument tip can be the result values (e.g., the resulting 30%, 42% and 58%), or derivative value from these result values such as the determination that the instrument tip is in the third branch. Although this example describes the use of the algorithm modules include EM-based algorithm, image-based algorithm, and robot-based algorithm, the estimation of the state for the instrument tip can also be provided based on different combinations of the various algorithms modules, including the path-based algorithm.

As above the estimated state may be represented in a number of different ways. For example, the estimated state may further include an absolute depth from airway to location of the tip of the instrument, as well as a set of data representing the set of branches traversed by the instrument within the tubular network, the set being a subset of the entire set of branches provided by the 3D model of the patient's lungs, for example. The application of probability distribution and confidence value on estimated states allows improved accuracy of estimation of location and/or orientation of the instrument tip within the tubular network.

As shown in FIG. 17B, the algorithm modules include an EM-based algorithm module 250, an image-based algorithm module 260, and a robot-based algorithm module 270. The algorithm modules shown in FIG. 17B is merely one example, and in alternative embodiments, different and/or additional algorithm modules involving different and/or additional navigation algorithms can also be included in the navigation module 205.

B.1. Branch Prediction System

The EM-based algorithm module 250 further includes an EM registration module 252, an EM localization module 254, and an EM branch prediction module 256. The EM registration module 252 may perform registration of EM coordinates to 3D model coordinates. The EM localization module 254 may determine an estimate of the position and orientation of the instrument. The EM branch prediction module 256 may determine a prediction as to which segment of the model the instrument will advance from a current segment in which the instrument is currently located.

Figure 17D:
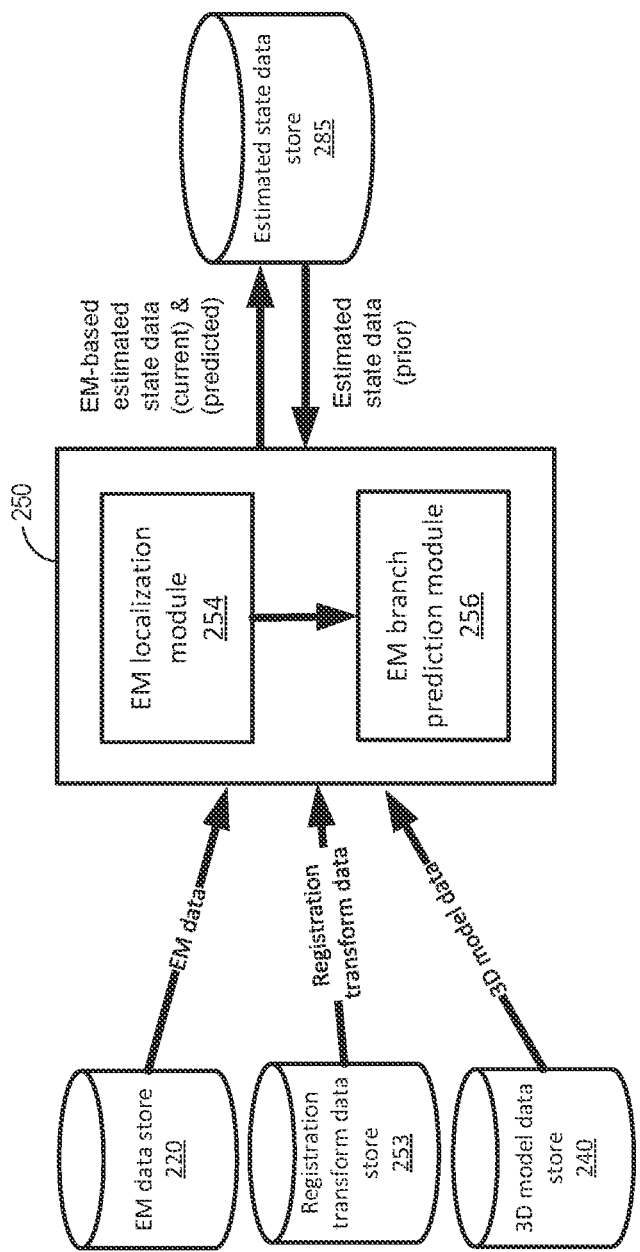
FIG. 17D illustrates an example location sensor-based branch prediction system in accordance with aspects of this disclosure.

FIG. 17D illustrates an example location sensor-based localization and branch prediction system in accordance with aspects of this disclosure. In particular, FIG. 17D shows a location sensor-based localization and branch prediction system that includes EM data store 220, registration transform data store 253, 3D model data store 240, EM localization module 254, EM branch predication module 256, and estimated state data store 285. The block diagram of the localization and branch prediction system is merely one example, and in other embodiments not shown, the localization and branch prediction system can include different and/or additional components, for example, in certain implementations the branch prediction system 210 may include one or more of image data store 220 and robot data store 230 in place of or in addition to EM data store 220.

The EM localization module 254 receives as inputs, estimated state data (prior) (e.g., bifurcation data) from the estimated state data store 285, the EM data from the EM data store 220, registration transform data from the registration transform data store 253, as well as 3D model data from the 3D model data store 240. Based on the received data, the EM localization module 254 determines an estimate of the position and orientation of the instrument tip relative to the 3D model of the tubular network and provides EM-based estimated state data (current) to the state estimator 280. As an example, the EM-based estimated state data may be represented as a probability distribution (e.g., a discrete distribution of 20%, 30% and 50% for three segments of a trifurcation, as described above). Additionally, when at a bifurcation as indicated by the received bifurcation data, the EM localization module 254 may compare the pitch and yaw of the tip of the instrument to the angles of each branch in the 3D model to estimate which branch has been selected by the user for traversal. The EM localization module 254 outputs the EM-based estimated state data (current) to the estimated data store 285 and the EM branch prediction module 256.

The EM branch prediction module 256 may determine a prediction as to which segment of the model the instrument will advance. For example, based on the determined current segment of the model in which the instrument is located and/or orientation data received from the orientation data store 289, the EM branch prediction module 256 may determine a prediction that the instrument will advance into each of the child segments of the current segment. There may be a number of different techniques which may be employed by the EM branch prediction module 256 for determining the prediction, which will be described in greater detail below. In some embodiments, the specific technique used by the EM branch prediction module 256 may depend on whether the location data has been registered to the model. The EM branch prediction module 256 may provide the determined prediction to the estimated state data store 285. In some embodiments as discussed above, the EM branch prediction module 256 may determine the predication based on orientation data received from the orientation data store 289. In other embodiments, the EM branch prediction module 256 may determine the predication based on position data from the position data store 287 or based on both the orientation data and the position data.

B.2. Example Route Taken by Instrument

For illustrative purposes, aspects of this disclosure related to location sensor-based branch prediction will be explained in the context of bronchoscopy and navigating portions of the bronchial luminal network. However, the present disclosure can also be applied to other luminal networks and other medical procedures.

Figure 18A:
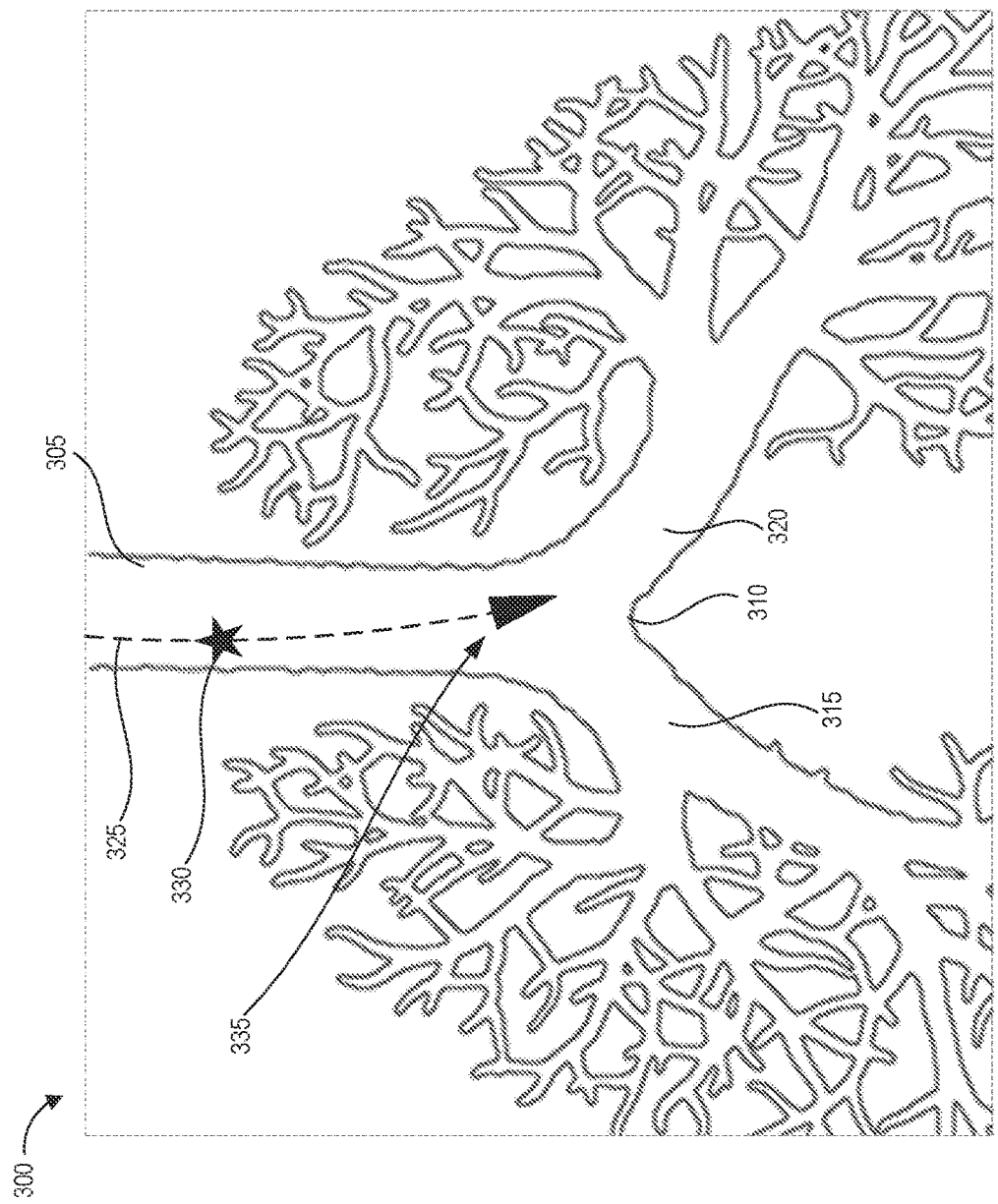
FIG. 18A is a flowchart illustrating an example method operable by a robotic system, or component(s) thereof, for unregistered location sensor-based branch prediction in accordance with aspects of this disclosure.

FIG. 18A illustrates an example luminal network in which location sensor-based branch prediction can be performed in accordance with aspects of this disclosure. In the embodiment of FIG. 18A, the illustrated luminal network 300 corresponds to airways of a patient's lungs and includes a first generation airway 305 (e.g., a trachea) which branches into two second generation airways 315 and 320 (e.g., primary bronchi) at a main carina 310. Assuming the patient is lying supine, the trachea 305 will branch into the patient's left bronchi 320 and the patient's right bronchi 315.

FIG. 18A also illustrates a route 325 along which the instrument may be driven as the instrument is navigated through the airways during a medical procedure. Two example tracked locations 330 and 335 of the instrument when driven along the route 325 are shown and will be referenced in discussing various embodiments. The location sensors may generate location data (not illustrated) representative of the tracked locations 330 and 335 within the location sensor coordinate system, as described in detail in connection with FIG. 18B below. Aspects of this disclosure may relate to the prediction of which airway the instrument will advance into between one of the second generation airways 315 and 320. As will be described in detail later, the processor may select an initial location 330 and a subsequent location 335 of the instrument for use in the branch prediction technique.

B.3. Example Location Data Generated During Procedure

Figure 18B:
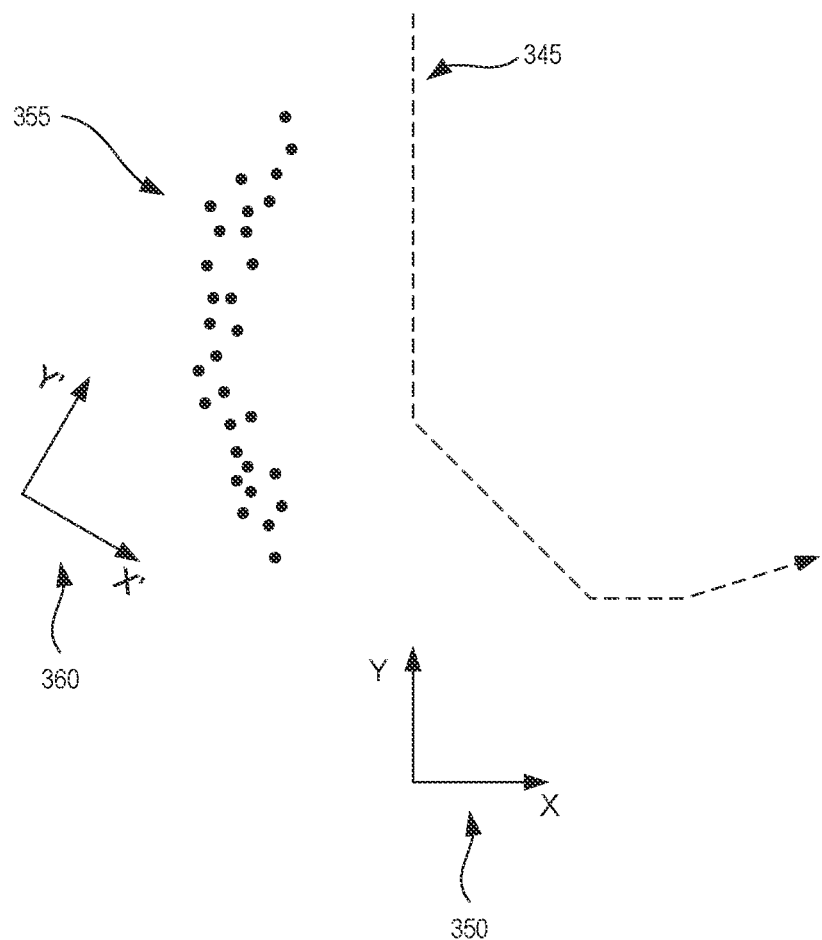
FIG. 18B illustrates an example set of location data points which may be generated by one or more location sensors as an instrument is driven through a luminal network in accordance with aspects of this disclosure.

FIG. 18B illustrates an example set of location data points which may be generated by one or more location sensors as an instrument is driven through a luminal network in accordance with aspects of this disclosure. In FIG. 18B, a navigation path 345 may be defined as a path along which the instrument is to be driven during the procedure. The navigation path 345 may be selected by a user prior to performing the procedure, generated by a path planning program, or the like. For the sake of convenience, FIG. 18B is illustrated in 2D, however, it is to be appreciated that this disclosure can be also applied to a 3D navigational path. The navigation path 345 may be defined with respect to a model coordinate system 350 in which a model (e.g., the skeleton-based model 500 of FIG. 20) of the patient's luminal network is defined.

During a procedure, the location sensors may generate a plurality of unregistered data points 355 which represent the tracked locations of the instrument as the instrument is navigated through the airways. The unregistered data points 355 may be defined with respect to a location sensor coordinate system 360. In the case of embodiments utilizing an EM sensors, the location sensor coordinate system 360 may be defined by or correspond to the EM field from the EM generator A navigation system (e.g., the localization system shown in FIG. 15) operating with a robotic system may determine a registration between the location sensor coordinate system 360 and the model coordinate system 350 which can be used to map the unregistered data points 355 into the model coordinate system 350. The registration may be stored in memory, for example, in the registration data store 225 of FIG. 17. One technique for registering the location sensor coordinate system 360 and the model coordinate system 350 may include selecting a transformation matrix which, when applied to the unregistered data points 355, minimizes the sum of the distances between the data points and the path 345. Once the registration is applied to the unregistered data points 355, the "registered" location data points may substantially align with the path 345.

B.4. Example Branch Prediction Technique

Figure 19:
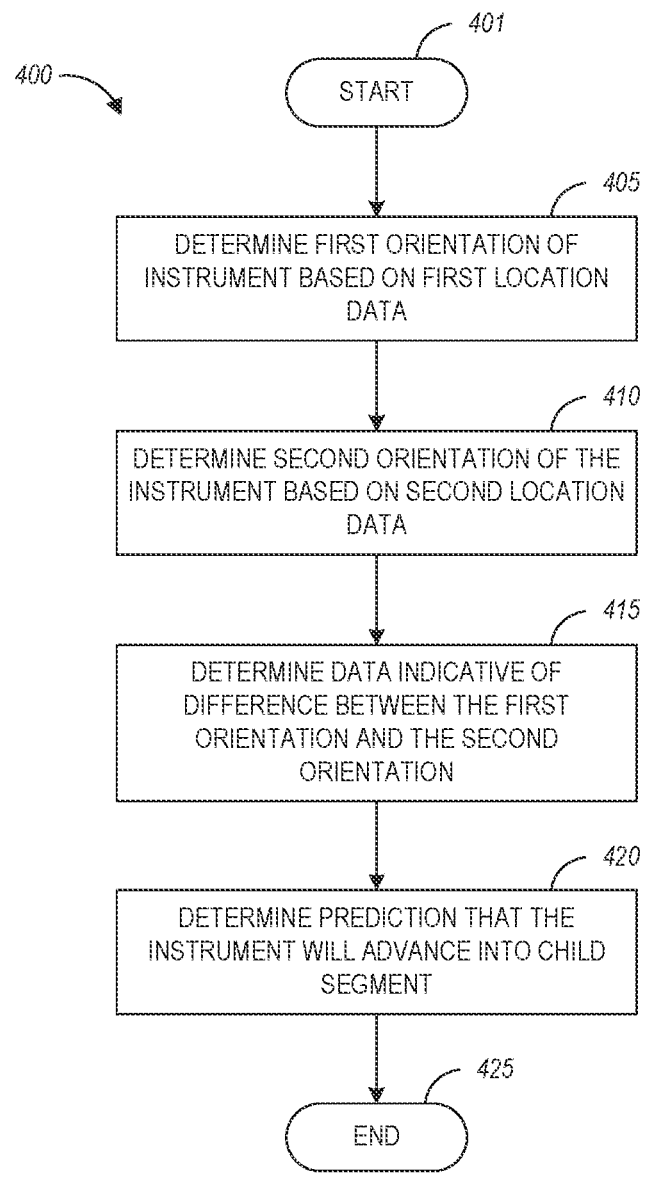
FIG. 19 illustrates an example luminal network in which location sensor-based branch prediction can be performed in accordance with aspects of this disclosure.

FIG. 19 is a flowchart illustrating an example method operable by a robotic system, or component(s) thereof, for location sensor-based branch prediction in accordance with aspects of this disclosure. For example, the steps of method 400 illustrated in FIG. 19 may be performed by processor(s) and/or other component(s) of a robotic system or associated system(s). For convenience, the method 400 is described as performed by the location sensor-based branch prediction system, also is also referred to simply as the "system" in connection with the description of the method 400.

At block 405, the location sensor-based branch prediction system determines a first orientation of an instrument based on first location data generated by a set of one or more location sensors for the instrument. The first location data may be indicative of the location of the instrument in a location sensor coordinate system at a first time. In certain embodiments, the location sensors may be located at or near a distal end of the instrument, and thus, the location data produced by the location sensors may be indicative of the location of the distal end of the instrument. In one embodiment, the first orientation of the instrument may correspond to the orientation of the instrument at an initial location, such as the initial location 330 of FIG. 18.

At block 410, the location sensor-based branch prediction system determines a second orientation of the instrument at a second time based on second location data generated by the set of location sensors. The distal end of the instrument may be located within a first segment of the model at the first time and the second time. The first segment may branch into two or more child segments. In the example embodiment illustrated in FIG. 18, the distal end of the instrument at the first time and the second time may respectively correspond to the initial location 330 and the subsequent location 335, each of which are located within the first generation airway 305 which branches into two second generation airways 315 and 320.

At block 415, the location sensor-based branch prediction system determines data indicative of a difference between the first orientation and the second orientation. This may include for example, determining the orientation of the instrument, based on unregistered location sensor data, at two successive points in time. Based on the difference between the orientations of the instrument while positioned in the current segment, the system may be able to predict into which of the two or more child segments the instrument is most likely to be advanced. That is, since the system has access to the orientation of each of the first generation airway 305 which branches into two second generation airways 315 and 320 from the model, the system may be able to predict which of the child segments the instrument is most likely to be advanced based on a change in the orientation of the instrument.

In one implementation, the location sensor-based branch prediction system may determine the difference between the initial orientation and a subsequent orientation by calculating the relative transformation matrix between the initial orientation and the subsequent orientation. The system may decompose the transformation matrix into the roll, pitch, and yaw angles, defining the orientation of the instrument in the location sensor coordinate system. Certain location sensor technologies (e.g., EM location sensors) which can be employed as the location sensor(s) may be substantially aligned with the patient in at least one angular degree of freedom when the patient lies supine for a given procedure (e.g., for a bronchoscopy procedure). In the EM implementation, an EM field generator may generate an EM field having an orientation that is defined with respect to the orientation of the EM field generator. Thus, by arranging the orientation of the EM field generator to be aligned with the patient, the system may be able to perform the branch prediction method 400 using only the yaw angle determined from the relative transformation matrix.

Since the orientation of the patient and the EM field may be known for a bronchoscopy procedure, the system may be able to determine a yaw angle between the initial orientation and the subsequent orientation based on the data generated by the EM sensor. The bifurcation of the trachea into the primary bronchi can thus be defined with respect to the yaw axis in the EM sensor coordinate system. Accordingly, when the instrument is located within the trachea 305 (see FIG. 18A), the yaw angle of the instrument determined based on the EM field may substantially align with the difference in orientation between the primary bronchi 315 and 320. Thus, the system may use a change in the yaw angle between the initial orientation and the subsequent orientation as the basis for updating the predication of the primary bronchi 315 and 320 into which the instrument is likely to be advanced.

In some embodiments, block 415 may also include the system determining the angle formed between the orientations of the child segments. The amount of change in the orientation of the distal end of the instrument may correspond to the angle formed between the child segments in order to redirect the insertion direction of the instrument from one of the child segments to the other. As described below, the system may use the angle formed between the child segments as a factor in determining whether to update the branch prediction and/or as a factor used in assigning probabilities to the child segments during branch prediction. It is to be appreciated that embodiments that select thresholds based on the angles formed between the child segments may be determined at design time (e.g., the threshold is a parameter selected by a designer of the system based on the angle) or during run-time (e.g., the system includes logic and data to dynamically determine the threshold either preoperatively or intra-operatively). It is also to be appreciated that run-time approaches may be impacted on the hardware and software of the system and the anatomy of the patient to accurately distinguish between the angles using the threshold.

At block 420, the location sensor-based branch prediction system determines a prediction that the instrument will advance into a first one of the child segments based on the data indicative of the difference. Depending on the embodiment, the prediction may include: an identification of the child segment the instrument is most likely to be advanced, a probability to each of the child segments that the instrument will be advanced into the corresponding child segment, an ordered list of the child segments from the highest probability to the lowest probability, etc. When the system has previously determined a predication that the instrument will advance into the child segments, the system may update the prediction based on the difference in orientation determined in block 415.

In embodiments where the system determines the angle between the child segments, the system may use the angle formed between the orientations of the child segments in determining the prediction. In other embodiments, the system may determine the prediction based on the difference between the orientation of the distal end of the instrument and the orientation of each of the child segments. In one embodiment, the system may assign a higher probability to a child segment that has a smaller difference in orientation from the orientation of the instrument than the remaining child segments.

In certain embodiments, the system may refrain from adjusting the probabilities of the instrument advancing into each of the child segments unless the orientation of the instrument has changed by more than a threshold level. The system may, in certain embodiments, adjust the threshold level based on the angle between the child segments. For example, the system may increase the threshold level when the angle between the child segments is greater than a first threshold angle and decrease the threshold level when the angle between the child segments is less than a second threshold angle. Once the system has determined a prediction that the instrument will advance into a given one of the child segments (e.g., based on the probability of advancing into the given one being greater than the probabilities for the other child segments), the system may subsequently determine the orientation of the instrument at a third time based on subsequent location data generated by the set of location sensors. The system may be configured to: calculate an angle between (i) the orientation at the third time (e.g., a time after the second time where the instrument is located at the subsequent location) and (ii) the initial orientation; and compare the calculated angle to a threshold angle value. The system may be further configured to update the probabilities of the instrument advancing into each of the child segments in response to the calculated angle being greater than the threshold angle value. Thus, in certain implementations, the system may not update the probabilities of the instrument advancing into each of the child segments unless the orientation of the instrument forms an angle with the initial orientation that is greater than the threshold angle value. The method 400 ends at block 425.

The above-described method 400 may be particularly advantageous when performed using unregistered location data. That is, since unregistered location data may not provide an exact mapping of the location and/or orientation of the instrument to the model coordinate system, the system may use the relative orientation of the instrument at two or more successive times to determine whether a change in the measured orientation of the instrument is consistent with the instrument being articulated towards one of the child segments. The detected change in the measured orientation of the instrument (e.g., within the location sensor coordinate system) may be consistent with a change in the physical orientation of the instrument to be pointed in a direction that is closer to the physical orientation of one of the child segments. In other words, the relative change in the orientation of the instrument in the location sensor coordinate system from the initial orientation to the subsequent orientation may still be indicative of a change in the direction of advancement of the instrument towards one of the child segments when determined using unregistered location data. Thus, since the location sensor coordinate system may not be registered to the model coordinate system during an initial phase of certain procedures, the method 400 can provide branch prediction during the initial phase, which can be used by a sensor fusion technique (e.g., localization system 90 of FIG. 15).

In one example, when the data indicative of a difference between the initial orientation and the subsequent orientation is consistent with the instrument being advanced or directed towards the patient's left primary bronchi (e.g., the second generation airway 320), the system may predict that the instrument will be advanced into the left primary bronchi rather than the right primary bronchi. Accordingly, the system may update the prediction for each child branch based on whether the change in the orientation is indicative of the instrument being advanced or directed towards or away from the corresponding child branch.

B.5. Selection of the Initial Location

As described above, the method 400 may include determining a first orientation of the instrument at block 405 when the instrument is located at an initial location. The location sensor-based branch prediction system may select the initial location of the instrument in response to initialization of the state estimation module 240. In certain embodiments, the location sensor-based branch prediction system may select the first indication of the location of the instrument produced by the state estimation module 240 after initialization as the initial location. However, in other embodiments, the system may select other locations (e.g., the second, third, etc. location of the instrument) produced by the state estimation module 240 as the initial location.

In some embodiments, the system may be configured to select the initial location of the instrument based on a determination that the orientation of the instrument at the initial location is substantially aligned with the orientation of the current segment (e.g., aligned with a longitudinal axis of the current segment). As used herein, the system may consider the orientation of the instrument to be substantially aligned with the orientation of the current segment when the difference between the orientations of the instrument and the current segment is less than a threshold difference. However, since the received location sensor data may be unregistered to the model coordinate system, the system may not be able to directly compare the orientation of the instrument to the orientation of the current segment.

In one implementation, the system may be configured to receive an indication from a user that the instrument is aligned with the current segment. The user may be able to confirm that orientation of the instrument is currently aligned with a first generation segment based on other sensors of the system (e.g., a camera located at the distal end of the instrument). In one implementation, the system may provide instructions to the user to drive the instrument to a defined position within the luminal network (e.g., the carina 310 of FIG. 18) and to retract the instrument by at least a defined distance from the defined position. The system may determine the location of the distal end of the instrument at the position before or after retraction, and set the orientation of the instrument at this point as the initial orientation which is substantially aligned with the orientation of the current segment.

In other implementations, the system may be configured or programmed to automatically select the initial location during the driving of the instrument without receiving user input. In one embodiment, the system may track the orientation of the instrument as the instrument is advanced through the current segment over a period of time and, in response to the orientation of the instrument being substantially unchanged for a threshold time period, the system may determine that the orientation of the instrument during the identified period is aligned with the orientation of the current segment. In some embodiments, the system may determine that the orientation of the instrument is substantially unchanged when a maximum difference between the measured orientations of the instrument over the time period is less than a threshold difference.

B.6. Confirmation of a Registration Process

In certain implementations, the system may be configured to perform a registration process in order to register the coordinate system of the location sensor(s) to the coordinate system of the model of the luminal network. The registration may be stored in a registration data store 225 as shown in FIG. 17. The registration process may include a process to facilitate the use of unregistered location data to determine the registration between the location sensor coordinate system and the model coordinate system. In certain embodiments, the registration process may be performed based on maintaining a history of the data received from the location sensor(s) and matching the shape formed by the location data history to the candidate paths along which the instrument can travel based on the model of the anatomy. The system may provide instructions to the user to drive the instrument along a predetermined registration path and track the position of the instrument based on the location sensors in response to the user driving the instrument along the registration path during the registration process. For certain procedures, the registration path may comprise a contra-lateral registration path defining the shape of the path along which the instrument is to be driven for the registration process. The contra-lateral registration path may include driving the instrument down a segment on a contra-lateral side of the luminal network with respect to the location of the target, retracting the instrument from the contra-lateral side, and driving the instrument along the lateral side of the luminal network along the path to the target (also referred to as a target path). Thus, the contra-lateral registration path may include driving the instrument along a contra-lateral branch of the luminal network outside the target path (e.g., along a branch that is on a contra-lateral side of the luminal network with respect to the target), returning the instrument back to the target path, and driving the instrument along a lateral branch which is located along a part of the target path.

In certain procedures, the target may include a nodule (or lesion) to which the instrument may be driven to facilitate diagnosis and/or treatment. Thus, the memory may store the target path to the target within the model and the contra-lateral registration path. During the registration process, the system may be configured to confirm whether the user is currently driving the instrument into the correct branch of the luminal network as defined by the contra-lateral registration path, based on the predictions of whether the instrument will advance down each of the child segments. Thus, the system may determine whether the instrument is located along the contra-lateral registration path based on the predictions. In one implementation, when approaching a bifurcation in the luminal network (e.g., the bifurcation near the primary bronchi), the system may compare the probability that the instrument will advance into the branch along the contra-lateral registration path to a threshold probability. When the probability is less than the threshold probability, the system may display an indication to the user that the user may not be driving towards the correct branch.

In another implementation, the system may determine that the instrument was advanced along the target path prior to being advanced down the contra-lateral registration path, which may be indicative of the user inadvertently driving the instrument along a path that does not correspond to the contra-lateral registration path used during the registration process. Since the contra-lateral registration path may require the instrument being driven down the contra-lateral path before being driven down the target path, the system may provide an indication that contra-lateral registration was unsuccessful in response to determining that the instrument was advanced along the target path prior to being advanced down the contra-lateral registration path.

The system may also be configured to display an indication of the location of the instrument with respect to the model during a given procedure to provide feedback to the user. Accordingly, the system may determine a position of the distal end of the instrument with respect to the model based on a plurality of sources of data indicative of the location of the instrument. In certain implementations, the system may determine the position of the distal end of the instrument based on one or more of: the location data received from the location sensors, a set of commands provided to control movement of the instrument, and prediction(s) that the instrument will advance into the child segments of the current segment. Thus, the prediction(s) determined via the method 400 of FIG. 19 may be one source of data that can be used by the system in localization and/or navigation of the instrument.

C. Registered Location Sensor-Based Branch Prediction.

After the system has performed a registration process, registering the location sensor coordinate system to the model coordinate system, the system may be able to use the data generated by the location sensor(s) to determine an indication of the location of the distal end of the instrument with reference to the model associated with the model coordinate system. Using the registered data location data, the system can produce a predication as to the child segment of the luminal network into which the instrument is most likely to be advanced. Depending on the implementation, the use of unregistered location sensor data may not provide sufficient accuracy for branch prediction in the luminal network once the instrument has been advanced into the luminal network beyond a certain distance. For example, once the instrument has been advanced into the primary bronchi, the system may not be able to performed branch prediction without registered location sensor data. Accordingly, aspects of this disclosure also relate to the use of registered location data for branch prediction.

Figure 20:
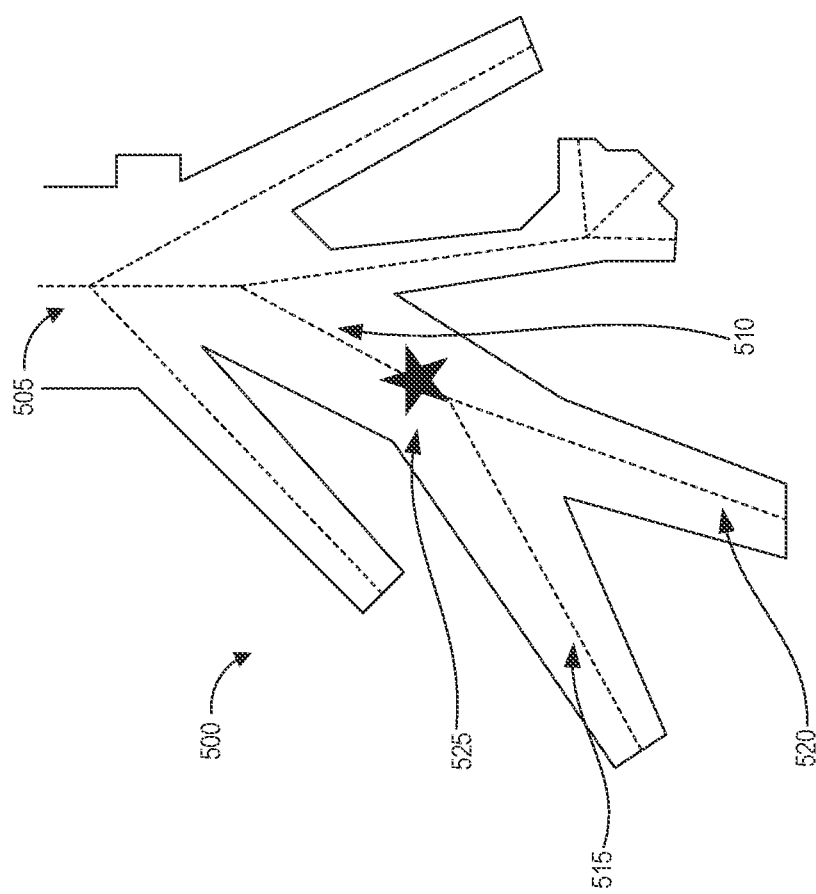
FIG. 20 is a flowchart illustrating an example method operable by a robotic system, or component(s) thereof, for registered location sensor-based branch prediction in accordance with aspects of this disclosure.

FIG. 20 illustrates an example skeleton-based model of a portion of a luminal network. In particular, the skeleton-based model 500 illustrates an implementation in which the luminal network is modelled as a "skeleton" 505 which may comprise a plurality of discrete segments, each corresponding to an individual lumen of the luminal network. The model 500 illustrated in FIG. 20 may be used by a localization system 90 (see FIG. 15) to calculate the position and orientation of the distal end of an instrument. Each segment of the skeleton 505 may be assigned a unique "segment ID" and each of the segments forming the skeleton 505 may be defined with respect to a center line of the corresponding lumen. During certain medical procedures, the instrument may be navigated through the luminal network for at least a portion of the procedure. In particular, at a given point in time, the distal end of the instrument 525 may be located within a current segment 510 of the model and the current segment 510 may branch or bifurcate into two child segments 515 and 520. As will be discussed in detail below, aspects of this disclosure relate to a branch prediction technique performed based on the orientation of the instrument when located within a current segment 510.

Figure 21:
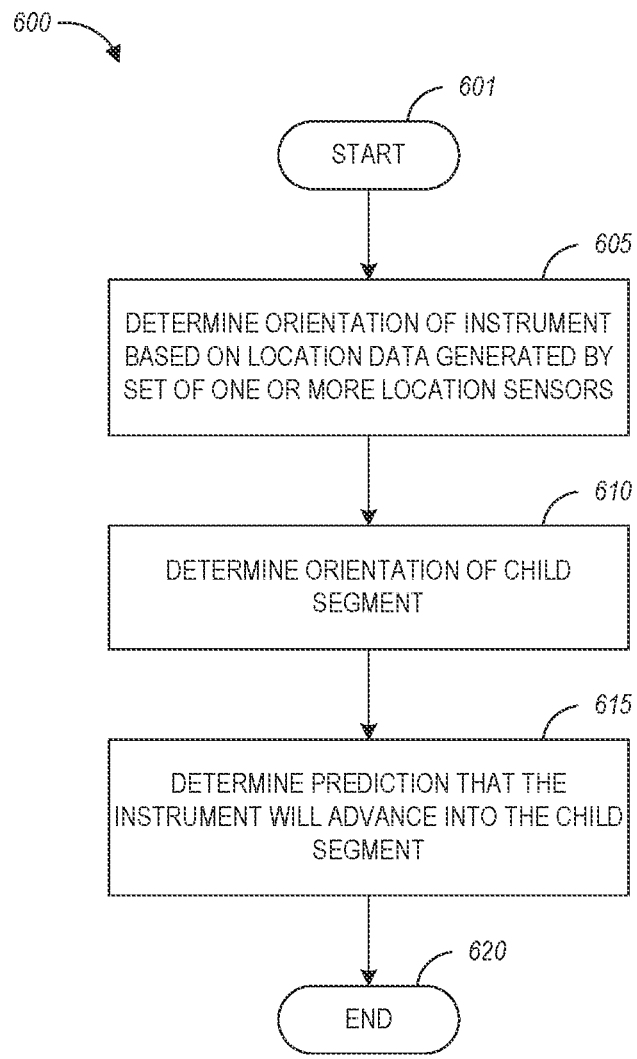
FIG. 21 is a flowchart illustrating an example method operable by a robotic system, or component(s) thereof, for location sensor-based branch prediction in accordance with aspects of this disclosure.

FIG. 21 is a flowchart illustrating an example method operable by a robotic system, or component(s) thereof, for registered location sensor-based branch prediction in accordance with aspects of this disclosure. For example, the steps of method 600 illustrated in FIG. 21 may be performed by processor(s) and/or other component(s) of a robotic system or associated system(s). For convenience, the method 600 is described as performed by the location sensor-based branch prediction system, also is also referred to simply as the "system" in connection with the description of the method 600. The robotic system may include at least one computer-readable memory having stored thereon a model of a luminal network of a patient.

At block 605, the location sensor-based branch prediction system determines an orientation of an instrument with respect to the model based on location data generated by a set of one or more location sensors for the instrument. In certain implementations, the location data includes registered location data received from the set of location sensors. At the time the location sensor data is received by the system, the location sensors may be registered to a model of the luminal network. Using the registered location data, the system may be able to determine the location of the distal end of the instrument with respect to the model based on the location data. In certain implementations, the system may employ a sensor fusion technique (e.g., by using localization system 90 of FIG. 15) which determines the location of the distal end of the instrument using multiple sources of data. Since the received location data is registered to the model, the system may be able to make a measurement of the location of the instrument with respect to the model.

In certain implementations, a distal end of the instrument may be located within a first segment of the model when the system determines the orientation of the instrument at block 605. In one embodiment, the distal end of the instrument 525 is located within a current segment 525 which includes two child branches 515 and 520 as shown in FIG. 20.

At block 610, the location sensor-based branch prediction system determines an orientation of a first one of the child segments. In the example of FIG. 20, the orientation of each of the child segments 515 and 520 may be determined based on the orientation of the corresponding segment of the skeleton 505 with respect to the model coordinate system. Depending on the implementation, the current segment may correspond to any one of the segments of the skeleton 505 which includes two or more child segments.

At block 615, the location sensor-based branch prediction determines a prediction that the instrument will advance into the first child segment based on the orientation of the instrument and the orientation of the first child segment. This may include, for example, the system determining the difference between the orientation of the distal end of the instrument 525 and the orientations of each of the child segments 515 and 520 in the FIG. 20 embodiment. The model may include data indicative of the orientations of each of the segments. In certain embodiments, the data indicative of the orientations of the segments may be included in the data representing the skeleton 505, in which the location, length, and orientation of each segment of the skeleton 505 may be defined in memory. Thus, the system may determine the orientation of the instrument in the model coordinate system using the registered location sensor data and compare the orientation of the instrument to the orientations of each of the child segments. The method ends at block 620.

Depending on the embodiment, the prediction may include: an identification of the child segment the instrument is most likely to be advanced, a probability to each of the child segments that the instrument will be advanced into the corresponding child segment, an ordered list of the child segments from the highest probability to the lowest probability, etc. Thus, in certain embodiments, the prediction may include data indicative of a probability that the instrument will advance into each of the child segments. In some implementations, the system may assign higher probabilities to child segments having a lower difference in orientation from the orientation of the instrument. Thus, the system may determine data indicative of a difference between the orientation of the instrument and the orientation of each of the child segments to aid in determining the corresponding probabilities.

In certain implementations, the system may further determine an angle between the orientation of the instrument and the orientation of each of the child segment. The angle between the orientation of the instrument and a given child segment may be indicative of the difference between the orientations. Thus, the system may be configured to assign a probability to a given child segment that is inversely proportional to the angle between the given child segment and the instrument. In one implementation, the system may determine the angle based on the dot product between the orientation of the instrument and the orientation of a given child segment. Since a smaller angle may be indicative greater alignment between the orientation of the instrument and a given child segment, the system may also use the inverse of the determined angle to calculate the probability for the given child segment.

The prediction may be used by the system as a source of data for a fusion technique (such as, e.g., the localization system 90 of FIG. 15) used to determine the location of the distal end of the instrument with respect to the model. In certain implementations, the system may determine the position of the distal end of the instrument based on one or more of: the location data received from the location sensor (s), a set of commands provided to control movement of the instrument, and the prediction(s) that the instrument will advance into each of the child segments.

In certain implementations, the system may apply an auxiliary technique for branch prediction in addition to the above-described orientation-based prediction. In one implementation, the auxiliary technique may include a location-based prediction which compares the location of the distal end of the instrument to the location of the beginning of each of the child segments. The system may determine an auxiliary prediction that the instrument will advance into each of the child segments based on the location of the distal end of the instrument. The prediction may be based on the location of the distal end of the instrument with respect to each of the child segments. Further details and examples of location-based prediction techniques which can be used as the auxiliary technique are described in U.S. Patent Publication No. 2017/0084027, referenced above. In one implementation, when the location senor data is indicative of the distal end of the instrument as being located closer to one child segment than another child segment, the system may assign a higher probability to the closer child segment than the farther child segment. For example, referring back to FIG. 20, when the distal end of the instrument 525 is closer to a first one of the child segments 515 than a second one of the child segments 520, the system may assign a higher probability to the first child segment 515. In some implementations, using the fusion technique, the system may determine the location of the distal end of the instrument based on both the orientation-based prediction technique and the auxiliary location-based prediction technique. The system may weight the results of each of the branch prediction techniques based on various factors, including the accuracies associated with each of the techniques, an error associated with a particular prediction, etc.

One advantage associated with orientation-based location sensor branch prediction over location-based branch prediction is that the orientation-based prediction may be performed continuously during the driving of the instrument through the luminal network. For example, a location-based branch prediction technique may not provide an accurate prediction unless the distal end of the instrument is within a threshold distance of the bifurcation of the current segment into the child segments. Since the location-based prediction technique relies on location sensor data, the location-based prediction technique may be susceptible to errors in the location sensor registration as well as to jitter in the location sensor data. Thus, when the instrument is relatively far away from the child segments, the distance between the instrument and each of the child segments may not be indicative of the child segment to which the user is driving the instrument towards. In contrast, the orientation of the instrument may be more strongly correlated with the child segment into which the user is driving the instrument even when the instrument is relatively far away from the bifurcation defined by the child segments. Accordingly, in some implementations, the orientation-based branch predication techniques described herein may be applied as the distal end of the instrument is advanced from a beginning of a current segment to an end of the current segment. In other embodiments, the system may apply the orientation-based branch prediction technique independent of the position of the distal end of the instrument within the current segment.

3. Implementing Systems and Terminology

Implementations disclosed herein provide systems, methods and apparatuses for location sensor-based branch prediction.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
a processor; and
at least one computer-readable memory in communication with the processor and having stored thereon a model of a luminal network of a patient, the memory further having stored thereon computer-executable instructions to cause the processor to:
determine an orientation of an instrument with respect to the model based on location data generated by a set of one or more location sensors for the instrument, a distal end of the instrument being located within a first segment of the model and the first segment branching into two or more child segments;
determine an orientation of a first one of the child segments and a second one of the child segments;
determine a prediction that the instrument will advance into the first child segment based on the orientation of the instrument and the orientation of the first child segment; and
responsive to an angle between the first child segment and the second child segment meeting a threshold, update the prediction that the instrument will advance into the first child segment.

2. The system of claim 1, wherein the prediction comprises data indicative of a probability that the instrument will advance into the first child segment.

3. The system of claim 1, wherein the memory further has stored thereon computer-executable instructions to cause the processor to:
determine data indicative of a difference between the orientation of the instrument and the orientation of the first child segment,
wherein the prediction that the instrument will advance into the first child segment is further based on the data indicative of the difference between the orientation of the instrument and the orientation of the first child segment.

4. The system of claim 1, wherein the memory further has stored thereon computer-executable instructions to cause the processor to:
determine an orientation of the second child segment; and
determine a prediction that the instrument will advance into the second child segment based on the orientation of the instrument and the orientation of the second child segment.

5. The system of claim 1, wherein the memory further has stored thereon computer-executable instructions to cause the processor to:
determine an angle between the orientation of the instrument and the orientation the first child segment, wherein the prediction that the instrument will advance into the first child segment is further based on the angle.

6. The system of claim 1, wherein the memory further has stored thereon computer-executable instructions to cause the processor to:
determine a position of the distal end of the instrument with respect to the model by analyzing the location data, a set of commands provided to control movement of the instrument, and the prediction that the instrument will advance into the first child segment.

7. The system of claim 6, wherein the memory further has stored thereon computer-executable instructions to cause the processor to:
determine a location of the distal end of the instrument with respect to the model based on the location data; and
determine an auxiliary prediction that the instrument will advance into the first child segment based on the location of the distal end of the instrument,
wherein determining the position of the distal end of the instrument with respect to the model is further based on analyzing the auxiliary prediction.

8. The system of claim 1, wherein the memory further has stored thereon computer-executable instructions to cause the processor to:
determine the prediction that the instrument will advance into the first child segment as the distal end of the instrument is advanced from a beginning of the first segment to an end of the first segment.

9. The system of claim 1, wherein the memory further has stored thereon computer-executable instructions to cause the processor to:
determine the prediction that the instrument will advance into the first child segment from the first segment independent of a position of the distal end of the instrument within the first segment.

10. The system of claim 1, wherein the prediction assigns a probability that is inversely proportional to a difference in orientation between the instrument and the orientations of the first child segment and the second child segment.

11. The system of claim 1, wherein the update is further responsive to a change in orientation, of the instrument, meeting an instrument threshold.

12. A non-transitory computer readable storage medium having stored thereon instructions that, when executed, cause at least one computing device to:
determine an orientation of an instrument with respect to a model based on location data generated by a set of one or more location sensors for the instrument, the model being stored in a memory and modelling a luminal network of a patient, a distal end of the instrument being located within a first segment of the model and the first segment branching into two or more child segments;
determine an orientation of a first one of the child segments and a second one of the child segments;
determine a prediction that the instrument will advance into the first child segment based on the orientation of the instrument and the orientation of the first child segment; and
responsive to an angle between the first child segment and the second child segment meeting a threshold, update the prediction that the instrument will advance into the first child segment.

13. The non-transitory computer readable storage medium of claim 12, wherein the prediction comprises data indicative of a probability that the instrument will advance into the first child segment.

14. The non-transitory computer readable storage medium of claim 12, further having stored thereon instructions that, when executed, cause at least one computing device to:
determine data indicative of a difference between the orientation of the instrument and the orientation of the first child segment,
wherein the prediction that the instrument will advance into the first child segment is further based on the data indicative of the difference between the orientation of the instrument and the orientation of the first child segment.

15. The non-transitory computer readable storage medium of claim 12, further having stored thereon instructions that, when executed, cause at least one computing device to:
determine an orientation of the second child segment; and
determine a prediction that the instrument will advance into the second child segment based on the orientation of the instrument and the orientation of the second child segment.

16. The non-transitory computer readable storage medium of claim 12, further having stored thereon instructions that, when executed, cause at least one computing device to:
determine an angle between the orientation of the instrument and the orientation the first child segment,
wherein the prediction that the instrument will advance into the first child segment is further based on the angle.

17. The non-transitory computer readable storage medium of claim 12, further having stored thereon instructions that, when executed, cause at least one computing device to:
determine a position of the distal end of the instrument with respect to the model by analyzing the location data, a set of commands provided to control movement of the instrument, and the prediction that the instrument will advance into the first child segment.

18. The non-transitory computer readable storage medium of claim 17, further having stored thereon instructions that, when executed, cause at least one computing device to:
determine a location of the distal end of the instrument with respect to the model based on the location data; and
determine an auxiliary prediction that the instrument will advance into the first child segment based on the location of the distal end of the instrument,
wherein determining the position of the distal end of the instrument with respect to the model is further based on analyzing the auxiliary prediction.

19. The non-transitory computer readable storage medium of claim 12, further having stored thereon instructions that, when executed, cause at least one computing device to:
determine the prediction that the instrument will advance into the first child segment as the distal end of the instrument is advanced from a beginning of the first segment to an end of the first segment.

20. The non-transitory computer readable storage medium of claim 12, further having stored thereon instructions that, when executed, cause at least one computing device to:
determine the prediction that the instrument will advance into the first child segment from the first segment independent of a position of the distal end of the instrument within the first segment.

21. A method of predicting movement of an instrument, comprising:

determining an orientation of an instrument with respect to a model based on location data generated by a set of one or more location sensors for the instrument, the model being stored in a memory and modelling a luminal network of a patient, a distal end of the instrument being located within a first segment of the model and the first segment branching into two or more child segments;

determining an orientation of a first one of the child segments and a second one of the child segments;

determining a prediction that the instrument will advance into the first child segment based on the orientation of the instrument and the orientation of the first child segment; and responsive to an angle between the first child segment and the second child segment meeting a threshold, updating the prediction that the instrument will advance into the first child segment.

22. The method of claim 21, wherein the prediction comprises data indicative of a probability that the instrument will advance into the first child segment.

23. The method of claim 21, further comprising:
determining data indicative of a difference between the orientation of the instrument and the orientation of the first child segment,
wherein the prediction that the instrument will advance into the first child segment is further based on the data indicative of the difference between the orientation of the instrument and the orientation of the first child segment.

24. The method of claim 21, further comprising:
determining an orientation of the second child segment; and
determining a prediction that the instrument will advance into the second child segment based on the orientation of the instrument and the orientation of the second child segment.

25. The method of claim 21, further comprising:
determining an angle between the orientation of the instrument and the orientation the first child segment,
wherein the prediction that the instrument will advance into the first child segment is further based on the angle.

26. The method of claim 21, wherein the location data is registered to a model coordinate system of the model.

27. The method of claim 21, further comprising:
determining a position of the distal end of the instrument with respect to the model by analyzing the location data, a set of commands provided to control movement of the instrument, and the prediction that the instrument will advance into the first child segment.

28. The method of claim 27, further comprising:
determining a location of the distal end of the instrument with respect to the model based on the location data; and
determining an auxiliary prediction that the instrument will advance into the first child segment based on the location of the distal end of the instrument,
wherein determining the position of the distal end of the instrument with respect to the model is further based on analyzing the auxiliary prediction.

29. The method of claim 21, further comprising:
determining the prediction that the instrument will advance into the first child segment as the distal end of the instrument is advanced from a beginning of the first segment to an end of the first segment.

30. The method of claim 21, further comprising:
determining the prediction that the instrument will advance into the first child segment from the first segment independent of a position of the distal end of the instrument within the first segment.

* * * * *